US010300296B2

(12) United States Patent
Ben-Yehuda et al.

(10) Patent No.: US 10,300,296 B2
(45) Date of Patent: May 28, 2019

(54) CAPSULE PHOTOTHERAPY

(75) Inventors: Sharon Ben-Yehuda, Rechovot (IL); Ram Ben-Yehuda, Rechovot (IL)

(73) Assignee: PhotoPill Medical Ltd., Rechovot (IL)

( * ) Notice: Subject to any disclaimer, the term of this patent is extended or adjusted under 35 U.S.C. 154(b) by 682 days.

(21) Appl. No.: 14/004,691

(22) PCT Filed: Mar. 7, 2012

(86) PCT No.: PCT/IL2012/050073
§ 371 (c)(1),
(2), (4) Date: Sep. 12, 2013

(87) PCT Pub. No.: WO2012/123939
PCT Pub. Date: Sep. 20, 2012

(65) Prior Publication Data
US 2014/0005758 A1    Jan. 2, 2014

Related U.S. Application Data

(63) Continuation-in-part of application No. PCT/IL2011/000257, filed on Mar. 17, 2011.

(60) Provisional application No. 61/314,762, filed on Mar. 17, 2010, provisional application No. 61/537,095, filed on Sep. 21, 2011.

(51) Int. Cl.
*A61N 5/06* (2006.01)
(52) U.S. Cl.
CPC ......... *A61N 5/0613* (2013.01); *A61N 5/0603* (2013.01); *A61N 5/0624* (2013.01); *A61N 2005/0609* (2013.01); *A61N 2005/0645* (2013.01); *A61N 2005/0659* (2013.01); *A61N 2005/0662* (2013.01)

(58) Field of Classification Search
CPC ................ A61N 2005/0626; A61N 2005/0627
USPC ...................................... 607/88–92
See application file for complete search history.

(56) References Cited

U.S. PATENT DOCUMENTS

| 4,217,045 A | 8/1980 | Ziskind |
| 5,464,436 A | 11/1995 | Smith |
| 5,604,531 A | 2/1997 | Iddan et al. |

(Continued)

FOREIGN PATENT DOCUMENTS

| EP | 1902664 | 3/2008 |
| JP | 2008-109954 | 5/2008 |

(Continued)

OTHER PUBLICATIONS

Supplementary European Search Report and the European Search Opinion dated Nov. 4, 2013 From the European Patent Office Re. Application No. 11755788.4.

(Continued)

*Primary Examiner* — John R Downey
(74) *Attorney, Agent, or Firm* — Vorys, Sater, Seymour and Pease LLP

(57) ABSTRACT

A swallowable capsule for providing phototherapy to a patient's gastrointestinal (GI) tract, the capsule including a power supply, one or more phototherapeutic light sources, a speed determination unit for calculating speed of movement of the capsule in the GI tract, and a controller unit for activating one or more of the one or more light sources for delivering a therapeutic illumination dose to a target site in the GI tract, based, at least in part, on a determined speed. Related apparatus and methods are also described.

24 Claims, 15 Drawing Sheets

(56) References Cited

U.S. PATENT DOCUMENTS

| | | | |
|---|---|---|---|
| 5,829,437 | A | 11/1998 | Bridges |
| 6,240,312 | B1 | 5/2001 | Alfano et al. |
| 6,273,904 | B1 | 8/2001 | Chen et al. |
| 6,383,177 | B1* | 5/2002 | Balle-Petersen ..... A61B 18/203 606/10 |
| 6,436,127 | B1* | 8/2002 | Anderson ........... A61B 5/0064 128/898 |
| 7,044,908 | B1 | 5/2006 | Montalbo et al. |
| 7,135,033 | B2* | 11/2006 | Altshuler ............ A61B 18/203 607/88 |
| 7,160,258 | B2 | 1/2007 | Imran et al. |
| 7,282,060 | B2* | 10/2007 | DeBenedictis ...... A61B 18/203 128/898 |
| 7,460,896 | B2 | 12/2008 | Iddan |
| 7,572,284 | B2 | 8/2009 | Abraham-Fuchs et al. |
| 7,625,338 | B2 | 12/2009 | Gilad et al. |
| 7,824,395 | B2* | 11/2010 | Chan .................... A61B 18/203 128/898 |
| 8,617,058 | B2 | 12/2013 | Arneson et al. |
| 8,911,360 | B2* | 12/2014 | Khait ..................... A61B 1/041 600/117 |
| 2001/0051766 | A1 | 12/2001 | Gazdzinski |
| 2002/0109774 | A1 | 8/2002 | Meron et al. |
| 2003/0214579 | A1* | 11/2003 | Iddan ................ A61B 1/00156 348/81 |
| 2004/0092825 | A1 | 5/2004 | Madar et al. |
| 2004/0122315 | A1 | 6/2004 | Krill |
| 2004/0133076 | A1 | 7/2004 | Kobayashi et al. |
| 2004/0249245 | A1 | 12/2004 | Irion |
| 2004/0254455 | A1 | 12/2004 | Iddan |
| 2005/0043586 | A1 | 2/2005 | Suzushima |
| 2005/0065441 | A1* | 3/2005 | Glukhovsky ......... A61B 5/065 600/476 |
| 2005/0096712 | A1 | 5/2005 | Abraham-Fuchs et al. |
| 2005/0143624 | A1 | 6/2005 | Iddan |
| 2005/0192478 | A1 | 9/2005 | Williams et al. |
| 2006/0030754 | A1 | 2/2006 | Iddan |
| 2006/0195014 | A1 | 8/2006 | Seibel et al. |
| 2008/0009751 | A1 | 1/2008 | Berndt |
| 2008/0033247 | A1 | 2/2008 | Wilson et al. |
| 2008/0058629 | A1 | 3/2008 | Seibel et al. |
| 2008/0068664 | A1 | 3/2008 | Gilad |
| 2008/0106596 | A1 | 5/2008 | Iddan et al. |
| 2008/0234569 | A1 | 9/2008 | Tidhar et al. |
| 2009/0177033 | A1 | 7/2009 | Hendriks et al. |
| 2009/0275923 | A1 | 11/2009 | Shimizu et al. |
| 2009/0318766 | A1 | 12/2009 | Rabinovitz et al. |
| 2010/0121420 | A1* | 5/2010 | Fiset ....................... A61N 5/06 607/94 |
| 2010/0222708 | A1 | 9/2010 | Hitchcock et al. |
| 2010/0240951 | A1 | 9/2010 | Catanese, III et al. |
| 2012/0226335 | A1 | 9/2012 | Surrenti et al. |
| 2012/0253204 | A1 | 10/2012 | Ben-Yehuda |
| 2012/0275683 | A1 | 11/2012 | Adler et al. |
| 2013/0013031 | A1 | 1/2013 | Ben-Yehuda et al. |
| 2014/0005758 | A1 | 1/2014 | Ben-Yehuda et al. |
| 2014/0081360 | A1 | 3/2014 | Ben-Yehuda et al. |

FOREIGN PATENT DOCUMENTS

| | | |
|---|---|---|
| JP | 2009-034291 | 2/2009 |
| JP | 2010-524557 | 7/2010 |
| KR | 893761 | 4/2009 |
| WO | WO 03/024328 | 3/2003 |
| WO | WO 03/084601 | 10/2003 |
| WO | WO 2007/113839 | 10/2007 |
| WO | WO 2008/012701 | 1/2008 |
| WO | WO 2009/031771 | 3/2009 |
| WO | WO 2009/032016 | 3/2009 |
| WO | WO 2009/102445 | 8/2009 |
| WO | WO 2011/055395 | 5/2011 |
| WO | WO 2012/123939 | 9/2012 |

OTHER PUBLICATIONS

International Preliminary Report on Patentability dated Sep. 26, 2013 From the International Bureau of WIPO Re. Application No. PCT/IL2012/050073.
Official Action dated Jan. 16, 2014 From the US Patent and Trademark Office Re. U.S. Appl. No. 13/494,199.
Official Action dated Mar. 12, 2014 From the US Patent and Trademark Office Re. U.S. Appl. No. 13/623,177.
Invitation Pursuant to Rule 62a(1) EPC dated Aug. 4, 2014 From the European Patent Office Re. Application No. 12757051.3.
Official Action dated Jul. 9, 2014 From the US Patent and Trademark Office Re. U.S. Appl. No. 13/634,555.
Applicant-Initiated Interview Summary dated Nov. 12, 2014 From the US Patent and Trademark Office Re. U.S. Appl. No. 13/634,555.
Supplementary Partial European Search Report and the European Search Opinion dated Dec. 4, 2014 From the European Patent Office Re. Application No. 12757051.3.
Official Action dated Feb. 27, 2015 From the US Patent and Trademark Office Re. U.S. Appl. No. 13/634,555.
Translation of Notification of Office Action dated Jul. 3, 2015 From the State Intellectual Property Office of the People's Republic of China Re. Application No. 201280018768.0.
Advisory Action Before the Filing of an Appeal Brief dated Aug. 27, 2015 From the US Patent and Trademark Office Re. U.S. Appl. No. 13/634,555.
Notice of Rejection dated Aug. 4, 2015 From the Japanese Patent Office Re. Application No. 2013-558570 and Its Translation Into English.
Official Action dated Jan. 4, 2016 From the US Patent and Trademark Office Re. U.S. Appl. No. 13/634,555.
Applicant-Initiated Interview Summary dated Aug. 22, 2013 From the US Patent and Trademark Office Re. U.S. Appl. No. 13/634,555.
International Preliminary Report on Patentability dated Sep. 27, 2012 From the International Bureau of WIPO Re. Application No. PCT/IL2011/000257.
International Search Report and the Written Opinion dated Aug. 5, 2011 From the International Searching Authority Re: Application No. PCT/IL2011/00257.
International Search Report and the Written Opinion dated Aug. 17, 2012 From the International Searching Authority Re: Application No. PCT/IL2012/050073.
Official Action dated Feb. 21, 2013 From the US Patent and Trademark Office Re. U.S. Appl. No. 13/634,555.
Official Action dated Apr. 25, 2013 From the US Patent and Trademark Office Re. U.S. Appl. No. 13/494,199.
Burton et al. "Relationship of Gastric Emptying and Volume Changes After Solid Meal in Humans", American Journal of Physiology Gastrointestinal and Liver Physiology, 289(2): G261-266, Aug. 2005.
Naumov et al. "Autonomous Device for Photostimulation of the Gastrointestinal Tract Immunity", Proceedings of SPIE, 3907, 433, Jan. 22, 2000.
Yu et al. "A Compartmental Absorption and Transit Model for Estimating Oral Drug Absorption", International Journal of Pharmaceutics, 186(2): 119-125, Sep. 20, 1999.
Yu et al. "Compartment Transit and Dispersion Model Analysis of Small Intestinal Transit Flow in Humans", International Journal of Pharmaceutics, 140: 111-118, 1996.
Communication Pursuant to Rules 70(2) and 70a(2) EPC dated Nov. 21, 2013 From the European Patent Office Re. Application No. 11755788.4.

* cited by examiner

CAPSULE PHOTOTHERAPY

RELATED APPLICATIONS

This application is a National Phase of PCT Patent Application No. PCT/IL2012/050073 having International filing date of Mar. 7, 2012, which is a continuation-in-part (CIP) of PCT Patent Application No. PCT/IL2011/000257 having International filing date of Mar. 17, 2011, and which claims the benefit of priority under 35 USC § 119(e) of U.S. Provisional Patent Application No. 61/537,095 filed on Sep. 21, 2011. PCT Patent Application No. PCT/IL2011/000257 claims the benefit of priority under 35 USC § 119(e) of U.S. Provisional Patent Application No. 61/314,762 filed on Mar. 17, 2010. The contents of the above applications are all incorporated by reference as if fully set forth herein in their entirety.

FIELD AND BACKGROUND OF THE INVENTION

The present invention, in some embodiments thereof, relates to an ingestible phototherapy device which may be used for treating diseases of the gastrointestinal tract, and in particular, for treating inflammatory bowel disease (IBD), using phototherapy.

Light therapy, conventionally referred to as "phototherapy", comprises exposing living tissue to light to treat a disease of the organism or tissue. The exposure is typically provided in accordance with a particular protocol tailored to the disease that defines spectrum and intensity of light used to illuminate the tissue and total energy deposited in the tissue by the light. The light may be generated using any of various suitable light sources, such as lasers, light emitting diodes (LEDs) and fluorescent lamps.

Phototherapy is generally applied to relatively easily accessible tissue regions, such as external regions of the skin and the mucosa lining the mouth or nose, and is used to treat acne, psoriases, eczema, vitiligo (in which damage to skin pigment cells results in white skin patches) and skin-based lymphoma, gingivitis, gum inflammations, oral ulcers, and allergic rhinitis.

Phototherapy for treatment of diseases of the gastrointestinal (GI) tract is generally not performed because of the relative difficulty in accessing GI tract tissue.

A similar-sounding but different field from phototherapy is Photodynamic Therapy (PDT). Most modern PDT applications involve three key components: a photo-sensitizer, a light source and tissue oxygen. The wavelength of the light source needs to be appropriate for exciting the photo-sensitizer to produce reactive oxygen species. The combination of these three components leads to the chemical destruction of any tissues which have either selectively taken up the photo-sensitizer or have been locally exposed to light. In understanding the mechanism of PDT it is important to distinguish it from other light-based and laser therapies such as laser wound healing and rejuvenation which do not require a photo-sensitizer.

International Patent Application Publication No. WO2008/012701 is entitled "Capsule camera with variable illumination of the surrounding tissue", and discloses an ingestible capsule and method for in vivo imaging and/or treatment of one or more diseased areas of interest within the gastrointestinal tract of an animal or human being. The capsule comprises an image sensor; a lens system for focusing images onto the image sensor; at least one light source for illumination of the tissue area of interest, the at least one light source optionally being capable of providing optical therapeutic treatment to the diseased areas; a variable lens system located in front of the at least one light source, wherein the variable lens system comprises beam steering means and focusing means for directing and focusing the light beams from the at least one light source onto the diseased tissue areas, a control unit in communication with the image sensor, the at least one light source, and variable lens system, a power source for powering the image sensor, the at least one light source and the control unit; and a non-digestible, transparent outer protective shell configured to pass through the gastrointestinal tract, housing within the image sensor, the lens system, the at least one light source, the variable lens system, the control unit and the power source.

An article entitled "Autonomous Device for Photostimulation of the Gastrointestinal Tract Immunity" by Sergey A. Naumov, Vladimir N. Dyrin, Sergey M. Vovk, Evgeny Y. Petrov, Vladimir V. Udut and Elena V. Borodulina, published in Proc. SPIE 3907, 433 (2000); doi:10.1117/12.386284, describes a very small optoelectronic device emitting light in the red and green band has been developed as a small capsule consisting of two semispheres connected with light-transmitted coupling. The device—a phototablet permits to irradiate all parts of the gastro-intestinal tract (GIT) including the immunocompetent formations of the small intestine —Peyer's patches responsible for production of secretory immunoglobulins A (IgA). The main mechanisms of realizing endogenic phototherapy using a phototablet begin functioning when irradiating both the walls of the GIT organs and its contents. The results of clinical trials of the phototablet testify to a favorable effect of endogenic therapy on the human organism in asthenic syndrome, some types of deficiency in the immunity function, in dysbioses, the syndrome of large intestine irritation, duodenostasis, etc. After endogenic phototherapy the patients had an increased level of lysozyme, leukocytes, a number of lactobacteria. There were no side effects when using a phototablet. Indications and contraindications for endogenic phototherapy were represented. Thus, the method of endogenic phototherapy allows us to have an effective and direct influence on the immunocompetent cells of GIT organs without medicamental agents and antigens that makes it possible to use the phototablet in medicine on a large scale.

U.S. Patent Application Publication No. 2009/0177033 of Hendriks et al., describes an application which relates to an ingestible capsule and method for in vivo imaging and/or treatment of one or more diseased areas of interest within the gastrointestinal tract of an animal or human being. The capsule comprises an image sensor; a lens system for focusing images onto the image sensor; at least one light source for illumination of the tissue area of interest, the at least one light source optionally being capable of providing optical therapeutic treatment to the diseased areas; a variable lens system located in front of the at least one light source, wherein the variable lens system comprises beam steering means and focusing means for directing and focusing the light beams from the at least one light source onto the diseased tissue areas, a control unit in communication with the image sensor, the at least one light source, and variable lens system, a power source for powering the image sensor, the at least one light source and the control unit; and a non-digestible, transparent outer protective shell configured to pass through the gastrointestinal tract, housing within the image sensor, the lens system, the at least one light source, the variable lens system, the control unit and the power source.

Additional background art includes:

an article titled: "Compartmental Transit and Dispersion Model Analysis of Small Intestine Transit Flow in Humans", by Lawrence X. Yu, John R. Crison and Gordon L. Amidon, published in International Journal of Pharmaceutics, Vol, 40; 1999;

an article titled: "Relationship of Gastric Emptying and Volume Changes After Solid Meal in Humans", by Duane D. Burton, H. Jae Kim, Michael Camilleri, Debra A. Stephens, Brian P. Mullan, Michael K. O'Connor, and Nicholas J. Talley, published in Am J Physiol Gastrointest Liver Physiol 289, 2005;

an article by Wirtz et al., published in Nature Protocols, Vol. 2, pp. 541-546, 2007;

PCT published patent application WO 2009/102445 of Bandy et al;

US published patent application 2008/0106596 of Iddan et al;

US published patent application 2004/0249245 of Trion;

US published patent application 2004/0106849 of Cho et al;

US published patent application 2003/0214579 of Iddan; and

U.S. Pat. No. 5,464,436 to Smith.

SUMMARY OF THE INVENTION

The present invention, in some embodiments thereof, is concerned with an ingestible capsule device suitable for phototherapy of the GI tract, particularly in cases of IBD, such as ulcerative colitis and Crohn's disease, Proctitis, Celiac, Diabetes type 1 and type 2, AIDS symptoms, and a phototherapy after retro-virus.

The terms PhotoPill and photopill may be used throughout the present specification and claims interchangeably with the term "phototherapy capsule" or with the term "capsule".

According to an aspect of some embodiments of the present invention there is provided a swallowable capsule for providing phototherapy to a patient's gastrointestinal (GI) tract, the capsule including a power supply, one or more phototherapeutic light sources, a speed determination unit for calculating speed of movement of the capsule in the GI tract, and a controller unit for activating one or more of the one or more light sources for delivering a therapeutic illumination dose to a target site in the GI tract, based, at least in part, on a determined speed.

According to some embodiments of the invention, if the speed determination unit determines a capsule speed which is substantially zero, the controller unit is configured to cause the controller unit to turn the light sources OFF.

According to some embodiments of the invention, the capsule controls the one or more phototherapeutic light sources in order to provide an effective dose to the target site of the GI tract.

According to some embodiments of the invention, the effective dose is computed, at least in part, based on speed of movement of the capsule in the GI tract.

According to some embodiments of the invention, the capsule controls the one or more phototherapeutic light sources based, at least in part, on the capsule measuring a speed of movement of the capsule in the GI tract.

According to some embodiments of the invention, the capsule adjusts an intensity of a light source based, at least in part, on the capsule measuring a speed of movement of the capsule in the GI tract.

According to some embodiments of the invention, the light sources emit light substantially mostly at one or more wavelengths in ranges selected from the group consisting of 400-480 nm, 610-750 nm, and 800-950 nm.

According to some embodiments of the invention, the light sources emit light centered at one or more wavelengths selected from the group consisting of 440 nm, 660 nm and 850 nm.

According to an aspect of some embodiments of the present invention there is provided a swallowable capsule for providing phototherapy to a patient's gastrointestinal (GI) tract, the capsule including a power supply, one or more phototherapeutic light sources, and a controller unit for activating one or more of the one or more light sources for delivering a therapeutic illumination dose to a target site in the GI tract, based, at least in part, on an expected speed of movement of the capsule at the target site of the GI tract.

According to an aspect of some embodiments of the present invention there is provided a method for intraluminal phototherapy of the gastrointestinal (GI) tract including swallowing a capsule including one or more phototherapeutic light sources capable of emitting light at wavelengths, doses and intensities suitable for providing a phototherapeutic effect, and a speed determination unit for calculating speed of movement of the capsule in the GI tract, and controlling activation of the light sources when the capsule is in proximity of one or more target sites in the gastrointestinal (GI) tract so as to provide an effective dose to the target site of the GI tract.

According to some embodiments of the invention, the effective dose is in the range of 0.25-0.5 Joule/cm$^2$.

According to some embodiments of the invention, the controlling includes controlling a Required_Power applied to the GI tract according to the following formula Required_Power=C*Dose/Intestine_Speed;

in which C is a constant programmed in the controller, Dose is a constant programmed in the controller, and Intestine_Speed is the speed of the capsule in the GI tract, and wherein the light sources are turned ON and OFF in order to provide approximately the Required_Power to the target sites in the GI tract.

According to some embodiments of the invention, the light sources are turned off when the capsule computes a speed of the capsule which indicates that the capsule has substantially stopped.

According to some embodiments of the invention, the light sources emit light substantially mostly at one or more wavelengths in ranges selected from the group consisting of 400-480 nm, 610-750 nm, and 800-950 nm.

According to some embodiments of the invention, the light sources emit light centered at one or more wavelengths selected from the group consisting of 440 nm, 660 nm and 850 nm.

According to some embodiments of the invention, the intraluminal phototherapy of the gastrointestinal (GI) tract is administered at a schedule selected from the group consisting of every other day, three times a week, and ranging from once a day to once a week.

According to some embodiments of the invention, the intraluminal phototherapy of the gastrointestinal (GI) tract is administered a plurality of times.

According to some embodiments of the invention, the intraluminal phototherapy of the gastrointestinal (GI) tract is administered a three times or more.

According to some embodiments of the invention, the method is used to treat inflammatory bowel disease selected from the group consisting of Crohn's disease, ulcerative colitis, and indeterminate colitis.

According to some embodiments of the invention, the method is used to promote healing of the intestinal mucosa and submucosal tissues.

According to an aspect of some embodiments of the present invention there is provided a method for treating GI tract lesions including swallowing a capsule including one or more phototherapeutic light sources capable of emitting light at wavelengths in ranges selected from the group consisting of 400-480 nm, 610-720 nm, and 800-950 nm, and controlling activation of the light sources when the capsule is in proximity of lesions in the gastrointestinal (GI) tract.

According to an aspect of some embodiments of the present invention there is provided a method for treating GI tract lesions including swallowing a capsule including one or more phototherapeutic light sources capable of emitting light at wavelengths consisting of one or more wavelengths in ranges selected from the group consisting of 400-480 nm, 610-720 nm, and 800-950 nm, and controlling activation of the light sources when the capsule is in proximity of lesions in the gastrointestinal (GI) tract.

According to an aspect of some embodiments of the present invention there is provided a method for intraluminal phototherapy of the gastrointestinal (GI) tract including a medical practitioner locating a diseased portion of the GI tract, administering a capsule to a patient for swallowing, the capsule including one or more phototherapeutic light sources capable of emitting light at wavelengths, doses and intensities suitable for providing a phototherapeutic effect, and a controller capable of activation of the light sources based on receiving a signal from an external unit, the medical practitioner detecting when the capsule is in proximity of the diseased portion of the GI tract, and the medical practitioner providing the signal to the controller when the capsule is in proximity of the diseased portion of the GI tract.

According to an aspect of some embodiments of the present invention there is provided a method for providing phototherapy to a stomach including swallowing a capsule including one or more phototherapeutic light sources capable of emitting light at wavelengths in ranges selected from the group consisting of 400-480 nm, 610-720 nm, and 800-950 nm, and activating the light sources when the capsule is in the stomach.

According to an aspect of some embodiments of the present invention there is provided a method for providing phototherapy to a colon including inserting a capsule into the colon, the capsule including one or more phototherapeutic light sources capable of emitting light at wavelengths in ranges selected from the group consisting of 400-480 nm, 610-720 nm, and 800-950 nm, and activating the light sources when the capsule is in the colon.

One aspect of the present invention relates to a phototherapy device for applying phototherapy to a patient's GI tract comprising a capsule, hereinafter also referred to as a "photopill", which the patient swallows so that it passes through his or her GI tract, and in passing, illuminates regions of the GI tract with therapeutic light.

In some embodiments of the invention, a patient optionally swallows medication and/or fluid, and allows the GI tract to clear before swallowing the capsule.

The present invention, in some embodiments thereof, is directed to a swallowable capsule device suitable for use in intraluminal phototherapy of the GI tract, wherein said capsule comprises one or more light sources, and optionally optical elements for shaping a light beam produced by the light source(s), such that the light source(s) and said optical elements are capable of delivering a therapeutic dose to a target site within the GI tract.

In some embodiments the aforementioned capsule has a shape similar to that of capsules produced for pharmaceutical use, with a smooth, rounded outline suitable for being swallowed by a human subject.

In some embodiments the aforementioned capsule has a radius somewhat smaller than a small intestine, which aids keeping the capsule from tilting in the GI tract.

In some embodiments of the invention, a light beam produced by the light source(s) is shaped by the optical elements such that the emitted light is transmitted out of the capsule in a direction which is essentially perpendicular to a longitudinal axis of the capsule, and/or approximately perpendicular to the direction of travel of the capsule. In such embodiments, the emitted light is, in use, directed approximately perpendicularly to the wall of the GI tract. Furthermore, an arrangement of the light sources and associated optical elements is such that the emitted light is transmitted outwards around the circumference of the capsule, thereby projecting a band of light that surrounds the capsule.

In some embodiments of the invention the emitted light is transmitted outwards around the entire circumference of the capsule.

In some embodiments of the invention the emitted light is projected in an essentially circular narrow band of light which surrounds the capsule. The 360 degree illumination pattern may be created in a number ways including—but not limited to—use of a plurality of light sources arranged around the circumference of the capsule, and/or use of reflective and/or refractive optical elements in order to change the direction in which the emitted light beams travel.

Any suitable light sources may be used in order to work the present invention, including lasers and light emitting diodes (LEDs). In some embodiments of the invention the light sources are optionally selected so as to emit light/photon radiation at a desired wavelength and/or wavelength band within the visible or near infra-red (NIR) ranges. Typically, by way of a non-limiting example, when treating GI tract lesions, the wavelength used is selected from one or more of the following ranges: 400-480 nm, 610-750 nm and 800-950 nm. Typical examples of emission wavelengths used include 440 nm (blue), 660 nm (red) and 850 nm (NIR). Additional wavelengths which are also expected to yield good results include: wavelengths ranging from 600 nm to 1000 nm, and a blue range from 440 nm to 490 nm. Combinations of the above ranges may also be effective. By way of a non-limiting example, white light, which includes all visible wavelengths, also includes the effective ones. By way of another non-limiting example, a combination of Red and Blue, or of NIR and Red and Blue. In some embodiments of the invention, different sources of light, emitting at different wavelengths, are incorporated in a single photopill device. In some embodiments of the invention, the phototherapy dose of treatment is a sum of the doses provided by each one of the wavelengths. As a result of concentration of the light, as the photopill moves through the GI tract the photopill provides concentrated therapeutic illumination to a relatively small section of the GI tract wall. Concentration of light from a photopill, in accordance with some embodiments of the invention, conserves optical energy provided by the photopill light source and improves efficiency with which the light is applied to walls of the GI tract. It is estimated that up to 3-5% of the power may be lost in passing through lenses, but as much as 15%, up to 30%, is gained by increased effectiveness of a concentrated beam, which provides an effective dose. A potential advantage of increased effectiveness is a savings in battery power.

In another embodiment of the present invention, an ingestible capsule (photopill) further comprises means for determining its direction, speed of movement and location as it travels through the GI tract. In some embodiments, the means are provided by an accelerometer. In some embodiments, the means are provided in the form of an optical motion sensing system, generally comprising an illumination source and one or more photo-detectors disposed within the capsule, such that said photodetectors are capable of detecting light signals that were emitted by said illumination source and reflected back towards the capsule by an external structure, such as the intestinal wall.

In some embodiments of the present invention, the photopill capsule further comprises control means such as one or more microprocessors (together with associated circuitry) for use in controlling at least some of the activities performed by the capsule including, but not limited to, initial triggering of a power supply; and/or initial triggering of a timer clock; and/or activation/deactivation of the therapeutic light source; and/or calculation of capsular speed; and/or calculation of direction and/or position, optionally from inputs provided by a motion detection system(s) and/or onboard timers; and/or calculation of therapeutic light intensity, and so on.

An advantage of some embodiments of the capsule device of the present invention is that all of the elements required for therapeutic light radiation and for the control and regulation of all of the various parameters related to said radiation may be contained within a single capsule, thereby obviating the need for ancillary control devices or assisting personnel.

In some embodiments of the invention, the photopill comprises a light source and a controller which turns on the light source to deliver therapeutic light at a desired location in the GI tract.

In some embodiments of the invention, the photopill comprises a light source and a controller which turns on the light source responsive to time measured by a timer, to deliver therapeutic light following a predetermined delay time. The predetermined delay time is determined responsive to a rate at which the photopill travels through a patient's GI tract and a location in the GI tract of a diseased region to be treated with phototherapy, so that the light source turns on to deliver phototherapy substantially only when it approaches and/or is near to a length of the GI tract in which the diseased region is located. Controlling the photopill to begin illumination only when it approaches and is near to a length of the GI tract that includes the diseased region improves energy efficiency of the photopill and reduces an amount of energy that must be supplied to the photopill to deliver a desired dose of therapeutic light to the diseased region.

In some embodiments of the invention, the controller turns off the light source when the photopill leaves the length of GI tract including the diseased region and is not in a position to illuminate the diseased region. In some embodiments of the invention, the photopill is used to treat a plurality of different diseased regions of the GI tract that are located in different spatially separated lengths of the GI tract. For each diseased region the controller turns on the light source when it approaches the diseased region and is in a position to illuminate it with therapeutic light and subsequently, except for optionally a last diseased region, turns off the light after it leaves the diseased region.

It is noted that the present invention is, of course, not limited to delivering phototherapeutic light to only limited lengths of the GI tract and if desired, a photopill in accordance with an embodiment of the invention can be configured to deliver therapeutic light to substantially all of a patient's GI tract.

In some embodiments of the invention, the photopill is contained in a package and comprises a switch that is used to turn on various elements within the capsule, including, but not limited to:

a timer, in order to initiate measuring time for determining a delay time and an exposure period, optionally starting when the photopill is removed from the package and is swallowed by the patient;

means for determining direction of movement, speed of movement, and location of the capsule, such as, by way of a non-limiting example, an accelerometer and/or an optical motion-sensing system.

Optionally, the switch comprises a magnetic proximity switch, which operates to turn on the timer when the photopill is distanced from a magnetic field generated by the package.

Optionally, the switch comprises a mechanical switch which is triggered by removal of the photopill from the package.

In a further embodiment, the initial triggering of the timer is effected by an operator-initiated squeezing or pressing of a mechanical switch element within the capsule.

In some embodiments of the invention, a phototherapy system comprises a set of photopills, each programmed with a different delay time and optionally a different exposure time. The set of photopills is used to provide phototherapy to different regions of a patient's GI tract while maintaining relatively low power consumption for each photopill.

In another aspect, the present invention provides a phototherapy system comprising an external beacon which transmits beacon signals such as radio or ultra sound beacon signals, and a photopill having a receiver for receiving the beacon signals. The beacon is located at a known location on a patient's body and locations of diseased regions of the patient's GI tract are correlated with characteristic features, such as for example frequency, polarization, and signal strength, of beacon signals transmitted by the beacon from the known location. After being swallowed by the patient, the photopill receives beacon signals and processes the signals to determine if the photopill is located in a region of the GI tract that is intended for phototherapy. If the photopill determines that it is located in such a region of the GI tract, the photopill turns on to illuminate the region with phototherapeutic light.

As mentioned hereinabove, in some embodiments of the invention, the photopill comprises an accelerometer for monitoring changes in speed with which the photopill travels through the GI tract. Optionally, changes in speed are used to control therapeutic light provided by the photopill. For example, such control is optionally useful when it is advantageous to provide a given quantity of therapeutic light to a particular region of the GI tract per unit area of the region.

In some embodiments of the invention, the photopill may be programmed to provide different amounts of therapeutic light to different areas within the GI tract. In some embodiments of the invention a travel speed of the capsule in the GI tract is known, and in order to provide an effective dose, different light intensities corresponding to different speeds are optionally provided. The intensity of therapeutic light provided by the photopill when traveling through the particular region is optionally controlled to be substantially proportional to the given quantity of therapeutic light to be delivered per unit area of the region, optionally taking into account a speed determined from a signal generated by an accelerometer. For example—for faster travel speeds with smaller tissue exposure time, higher power is required to maintain a constant desired dosage of therapeutic light. As disclosed hereinabove, other motion-detecting means, such as optical means, may be used in place of, or in addition to, an accelerometer.

In some embodiments of the invention, changes in speed are used to determine where the photopill is located in the GI tract. Optionally, location is determined by double-integrating acceleration determined responsive to measurements by an accelerometer, over time, to determine distance traveled through the GI tract.

In some embodiments of the invention, a substantial change in speed, optionally indicated by acceleration measurements provided by the accelerometer, is used to determine location. For example, material propagating through the GI tract moves more slowly in the Cecum than in the small intestine. As a result, a substantial decrease in speed of travel of the photopill indicated by accelerometer signals, indicating substantial deceleration, is optionally used to determine when the photopill reaches the Cecum.

In some embodiments of the invention, a swallowable capsule for providing phototherapy to a region of a patient's gastrointestinal (GI) tract is provided, the capsule comprising: at least one light source controllable to generate light for phototherapy; and a controller that turns on the at least one light source at a phototherapy start time to illuminate a portion of the GI tract that includes at least a portion of the region.

Optionally, when the controller turns on the at least one light source at the phototherapy start time, the capsule is located near to a position in the GI tract at which light from the light source can illuminate the region. Additionally or alternatively the near position is optionally within 10 cm of the region. Optionally, the near position is within 5 cm of the region. Optionally, the near position is within 2 cm of the region. In some embodiments of the invention, the controller comprises a timer.

Optionally, the phototherapy start time is a time determined relative to a clock-on time, at which clock-on time the timer begins measuring time to determine the phototherapy start time. Optionally, the capsule is contained in a package and the clock-on time is a time determined by removing the capsule from the package. The swallowable capsule optionally comprises a switch which is operated by removal of the capsule from the package to set the clock-on time. Optionally, the switch is magnetically operated. Optionally, the package comprises a magnet which generates a magnetic field, and the switch is operated to set the clock-on time responsive to changes in the magnetic field at the capsule caused by removal of the capsule from the package.

In some embodiments of the invention, the switch comprises a push-button that is operated to set the clock-on time. Optionally, the push-button is mechanically operated to operate the switch. Optionally, the package comprises a protuberance and the push-button is depressed by the protuberance when the capsule is in the package and is released to operate the switch and set the clock-on time when the capsule is removed from the package.

In some embodiments of the invention, the controller operates the switch to set the clock-on time responsive to a change in a feature of the ambient environment of the capsule. Optionally, the feature is temperature. Additionally or alternatively the feature optionally comprises light. In some embodiments of the invention, the feature comprises pH. In some embodiments of the invention the feature comprises moisture.

In some embodiments of the invention, the capsule receives light signals from outside the body. The light signals optionally serve as to receive communications from outside the body. The communications optionally include activation commands, and/or programming parameters in the capsule. The parameters may include delay times, start and stop times, and phototherapeutic light intensity, In some embodiments of the invention, the phototherapy start time is a time delayed by a predetermined delay time from the clock-on time. Optionally, the predetermined delay time is determined responsive to location of the region and a speed with which the capsule travels through the GI tract to the region.

In some embodiments of the invention, the controller is configured to receive a beacon signal and determines the phototherapy start time responsive to a beacon signal generated by a beacon. Optionally, the beacon signal comprises a magnetic field.

Optionally, the controller determines the phototherapy start time responsive to strength of the magnetic field.

In some embodiments of the invention, the beacon signal comprises an acoustic signal.

In some embodiments of the invention, the beacon signal comprises an ultrasound signal.

In some embodiments of the invention, the beacon signal comprises an RF signal. Additionally or alternatively, the beacon signal is optionally characterized by frequency that is a function of direction relative to a location of the beacon.

Optionally, the controlled determines the phototherapy start time responsive to the frequency.

In some embodiments of the invention, the controller determines the phototherapy start time responsive to intensity of the beacon signal.

In some embodiments of the invention, the controller turns off the at least one light source at a phototherapy stop time subsequent to the phototherapeutic start time following a predetermined exposure period during which it illuminates the GI tract with phototherapeutic light.

In some embodiments of the invention, the controller determines a plurality of phototherapy start times.

In some embodiments of the invention, a swallowable capsule comprises an accelerometer that generates acceleration signals responsive to acceleration of the capsule. Optionally, the controller receives the acceleration signals generated by the accelerometer. Optionally, the controller adjusts intensity of therapeutic light provided by the at least one light source responsive to the acceleration signals. Additionally or alternatively, the controller optionally determines a distance traveled by the capsule in a patient's GI tract responsive to the acceleration signals. Optionally, the controller turns on the at least one light source responsive to the determined distance.

There is further provided in accordance with an embodiment of the invention, a swallowable capsule for providing phototherapy to a region of the gastrointestinal (GI) tract of a patient, the capsule comprising: at least one light source controllable to generate light for phototherapy; and a light director that receives light from the at least one light source and concentrates the light within an essentially circular band shaped volume.

In another aspect the present invention is also directed to a method for intraluminal phototherapy of the gastrointestinal tract in a patient in need of such treatment comprising the steps of:

a) providing a swallowable capsule as disclosed hereinabove and described in more detail hereinbelow; and b) oral administration of the capsule to said patient.

The term "intraluminal phototherapy" as used herein refers to the use of light-irradiation treatment in order to treat lesions and/or promote tissue healing from within the lumen of the GI tract. The methods provided in some embodiments of the present invention are thus applicable to the treatment and healing of conditions of all tissues accessible from the GI lumen including the intestinal mucosa and sub-mucosal tissues.

In some embodiments of the invention, the patient self-administers the capsule device.

In one preferred embodiment of this aspect of the invention, the method is used to treat IBD. The presently-disclosed method may be used to treat all types of IBD, including Crohn's disease, ulcerative colitis, Proctitis, Celiac, Diabetes type 1, Diabetes type 2, AIDS symptoms, and indeterminate colitis. The treatment improves a GI tract, including situations where the above-mentioned diseases cause problems in the GI tract due to improper blood flow and/or damage to the mucosa.

In another preferred embodiment, the method of the invention is used to promote, encourage and accelerate healing of the intestinal mucosa and underlying tissues.

In one preferred embodiment of the invention, the method is used to treat lesions and/or promote healing of tissues that are present in the small intestine.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard disk, and/or flash memory, and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

In the drawings:

Figure 1:
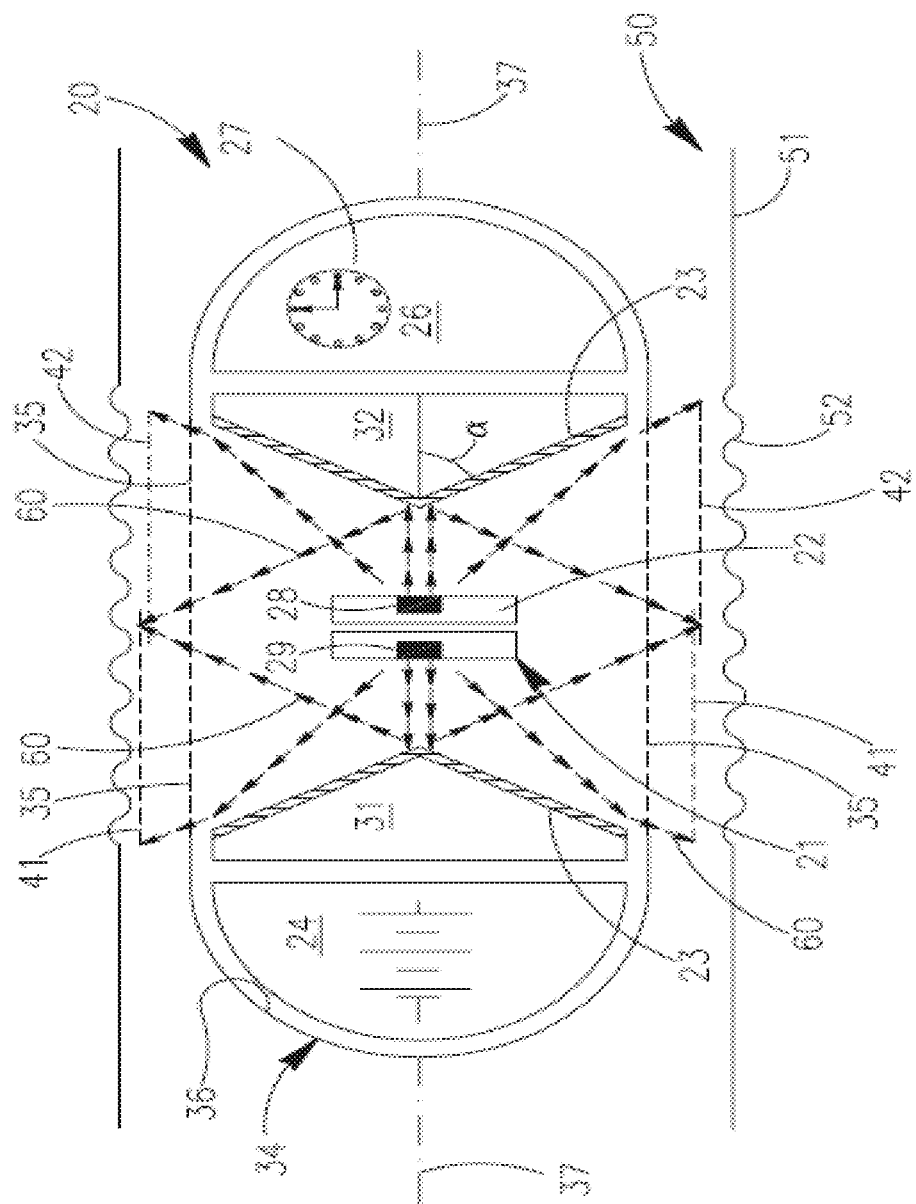
Figure 2:
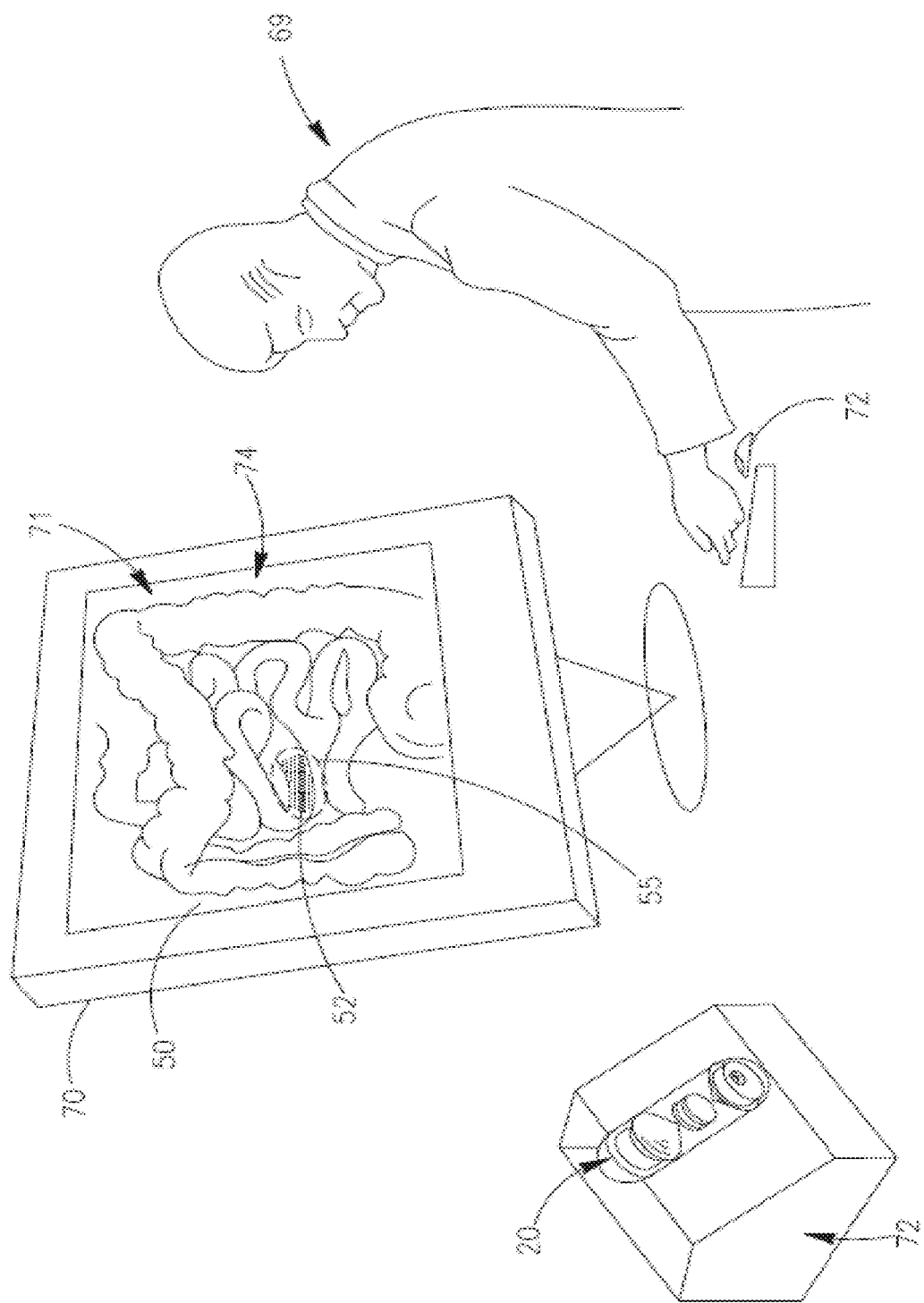
Figures 3A, 3B:
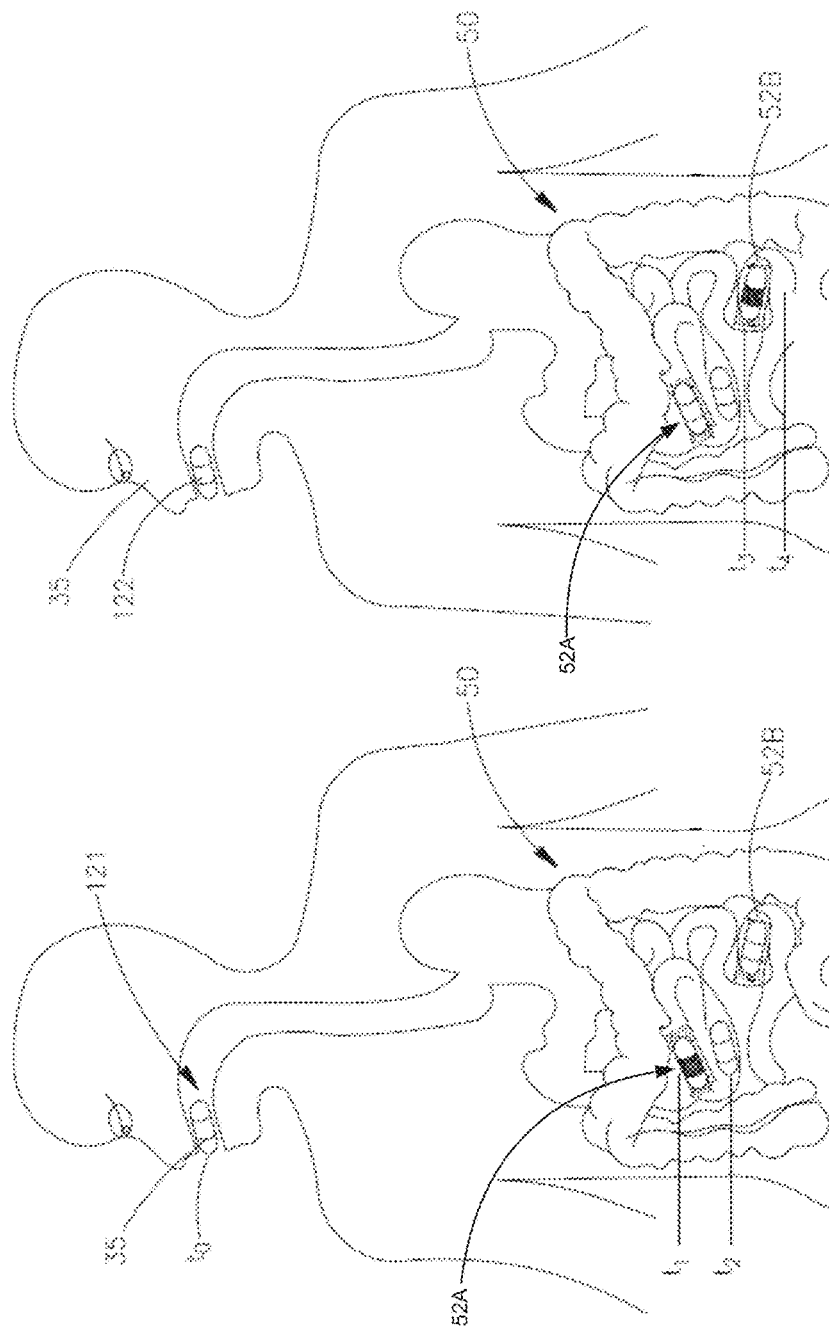
Figure 4:
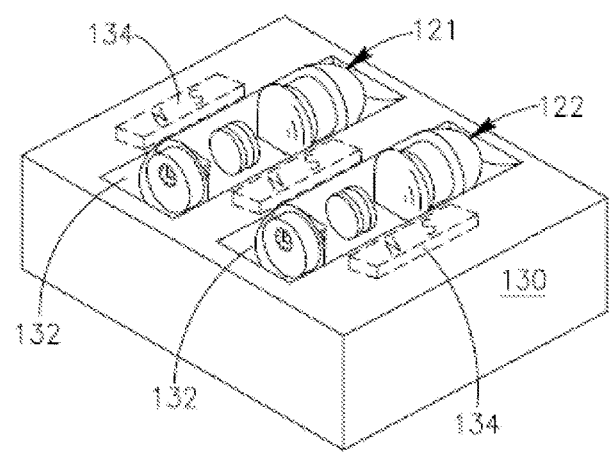
Figure 5:
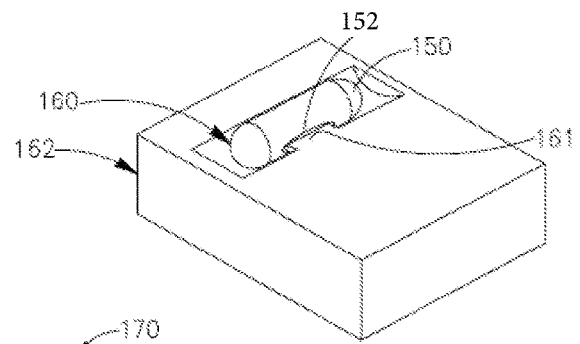
Figure 6:
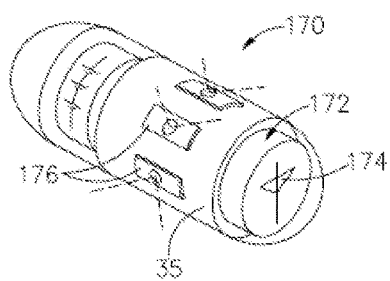
Figure 7:
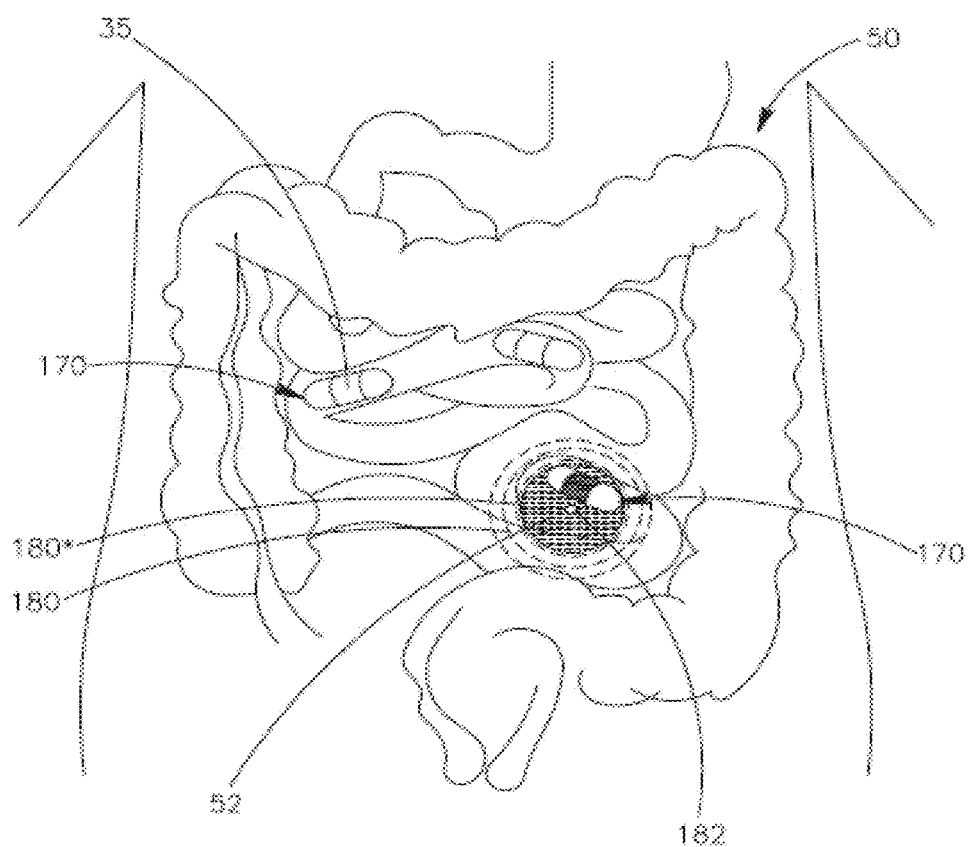
Figure 8:
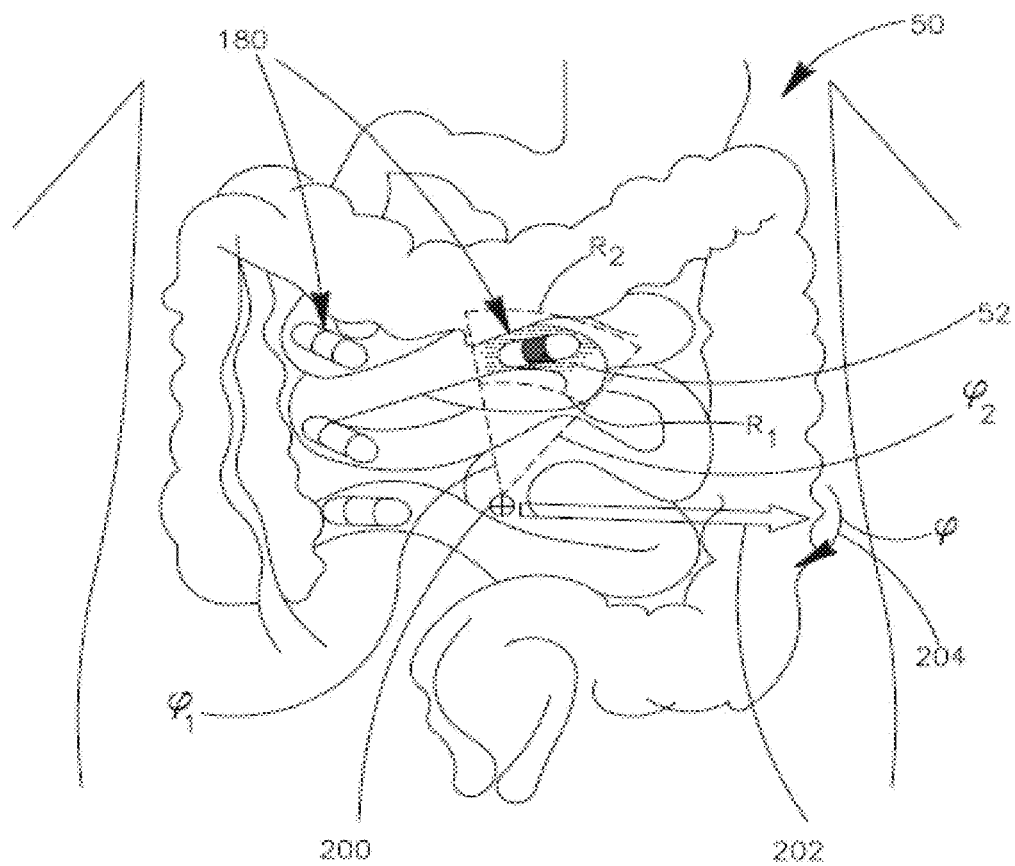
Figure 9:
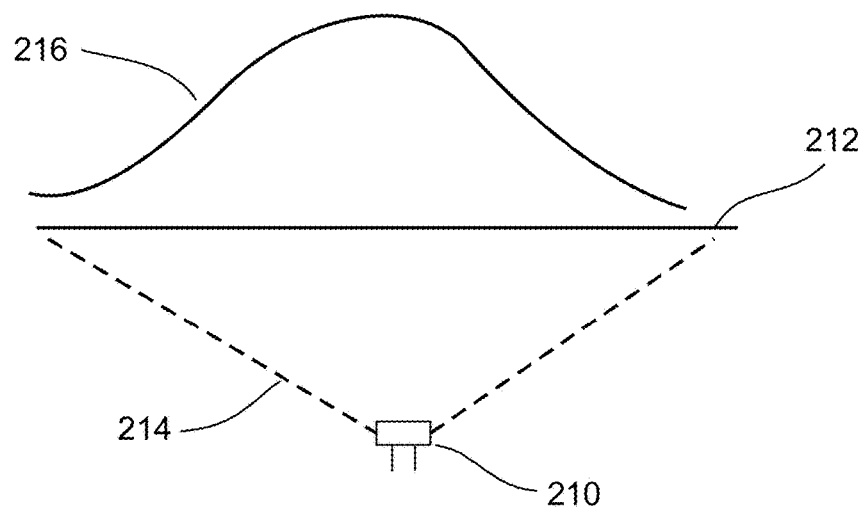
Figure 10:
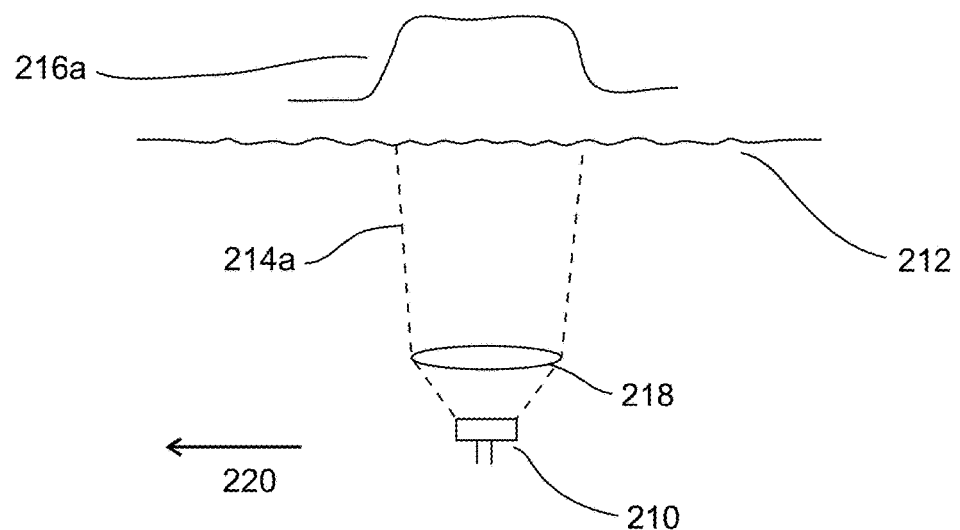
Figure 11:
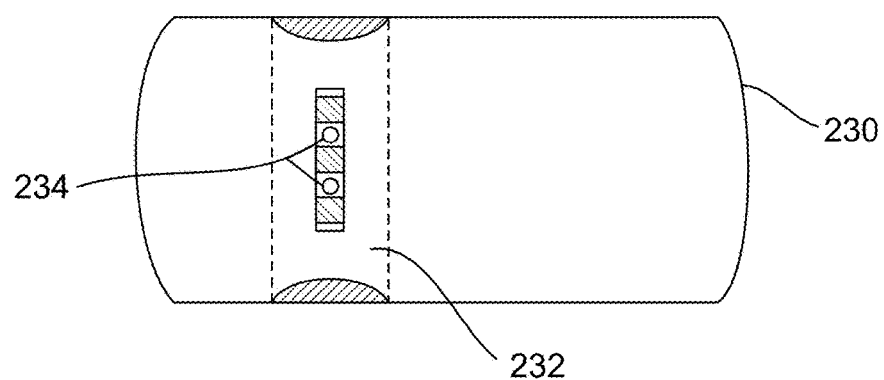
Figure 12:
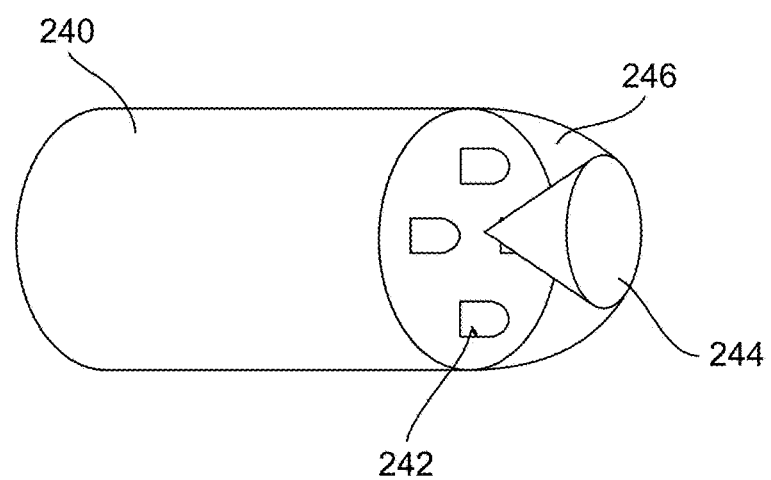
Figure 13:
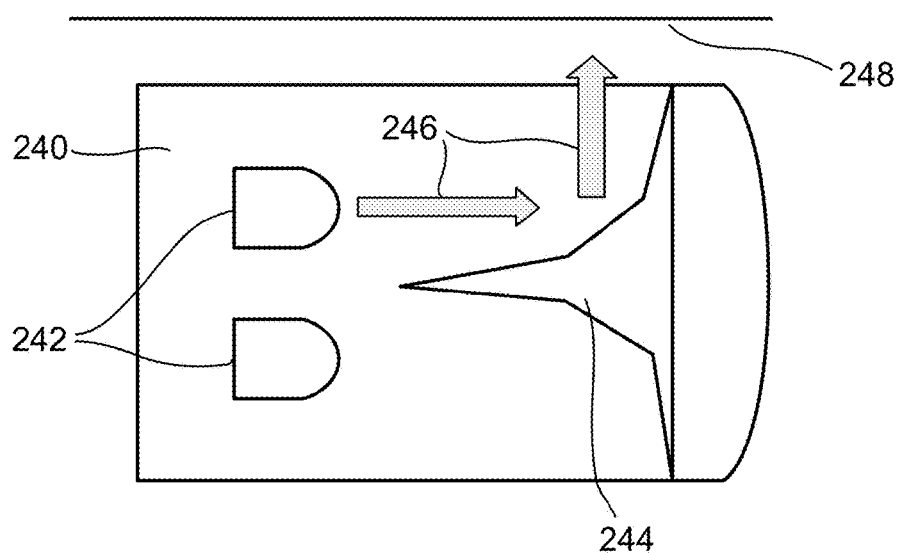
Figure 14:
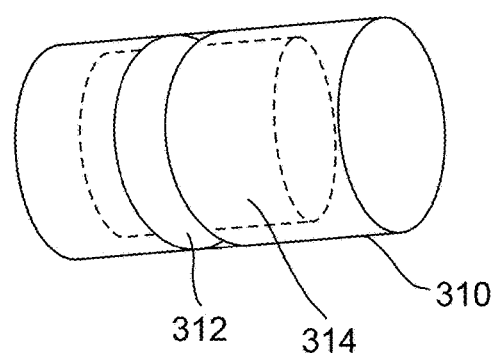
Figure 15:
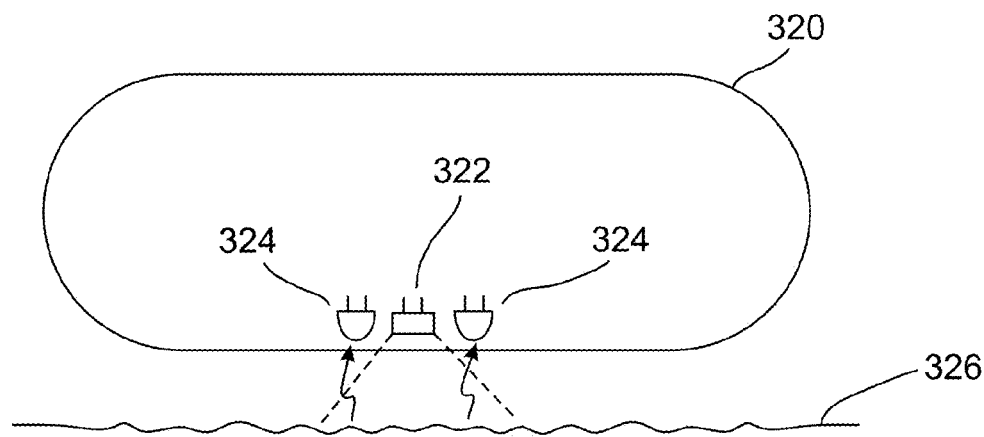
Figure 16:
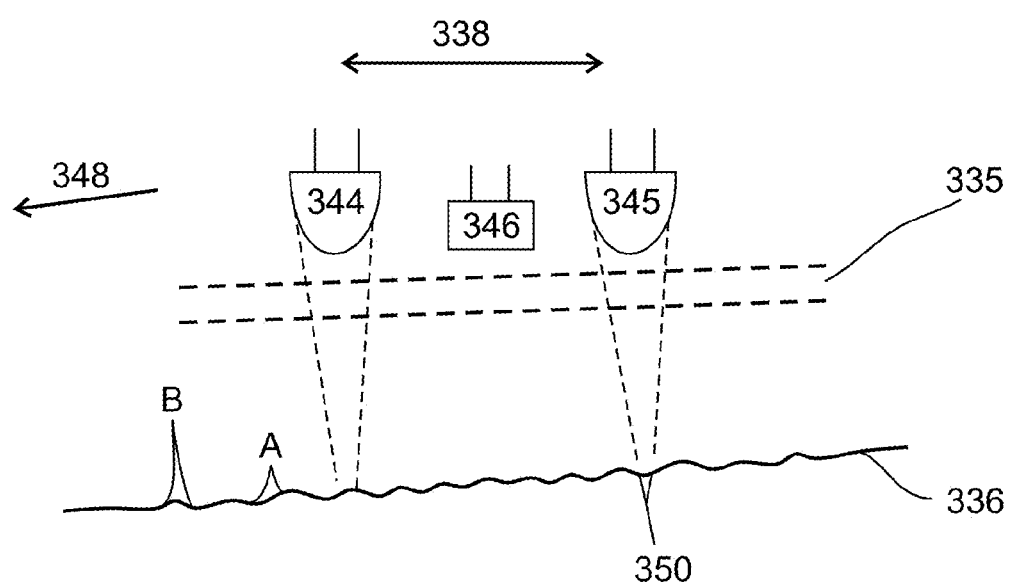
Figure 17:
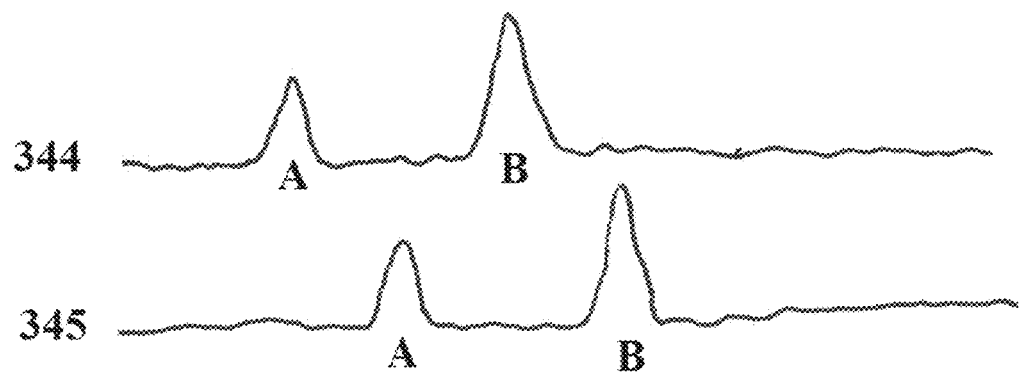
Figure 18:
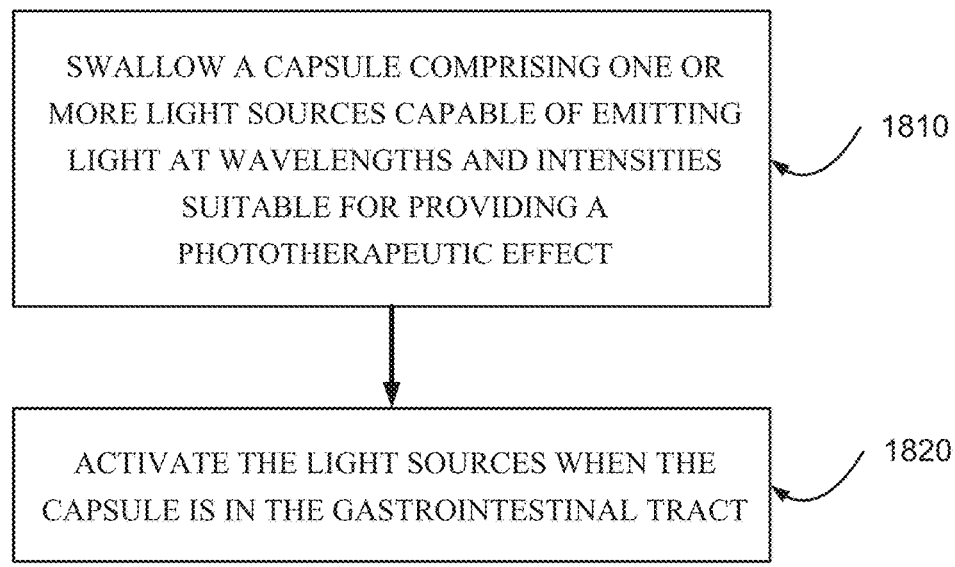
Figure 19A:
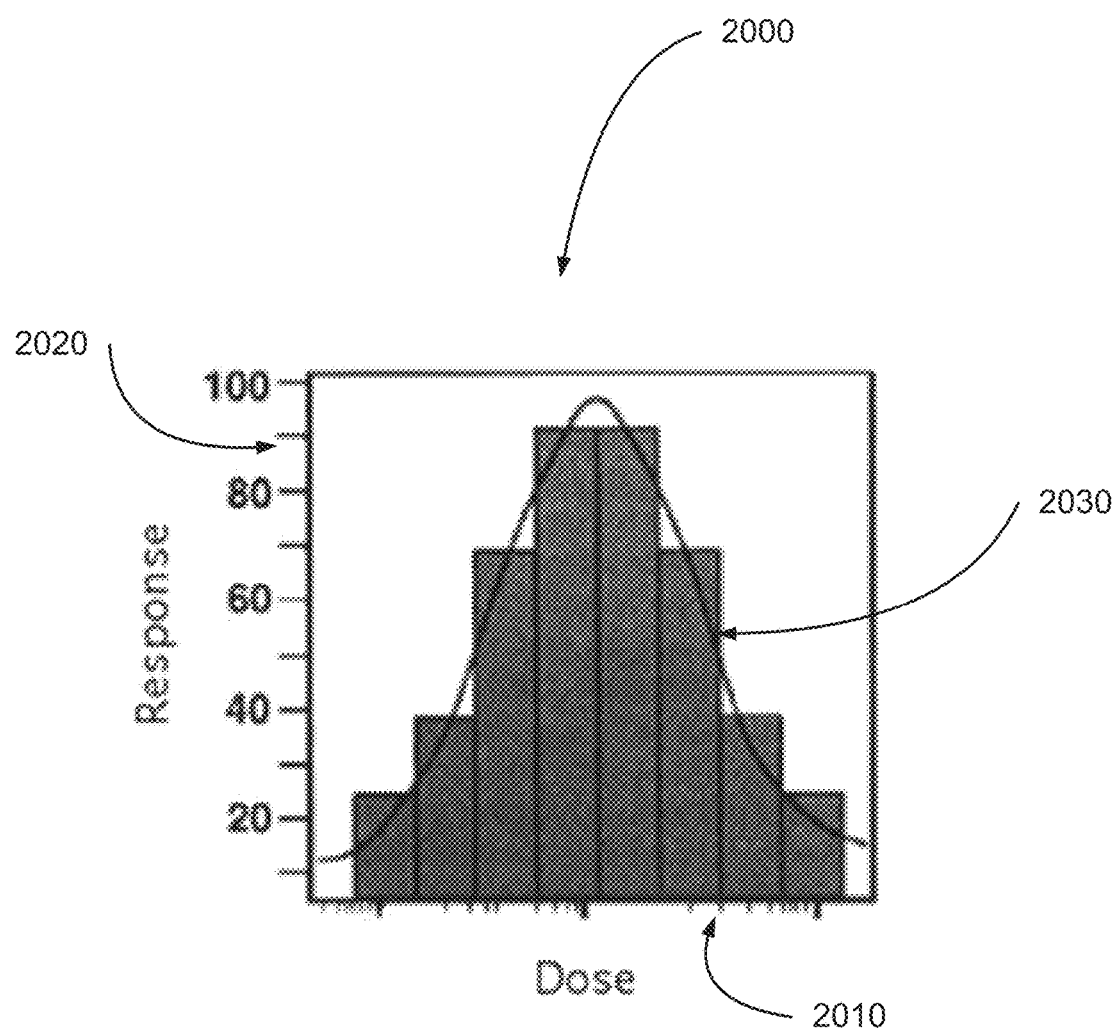
Figure 19B:
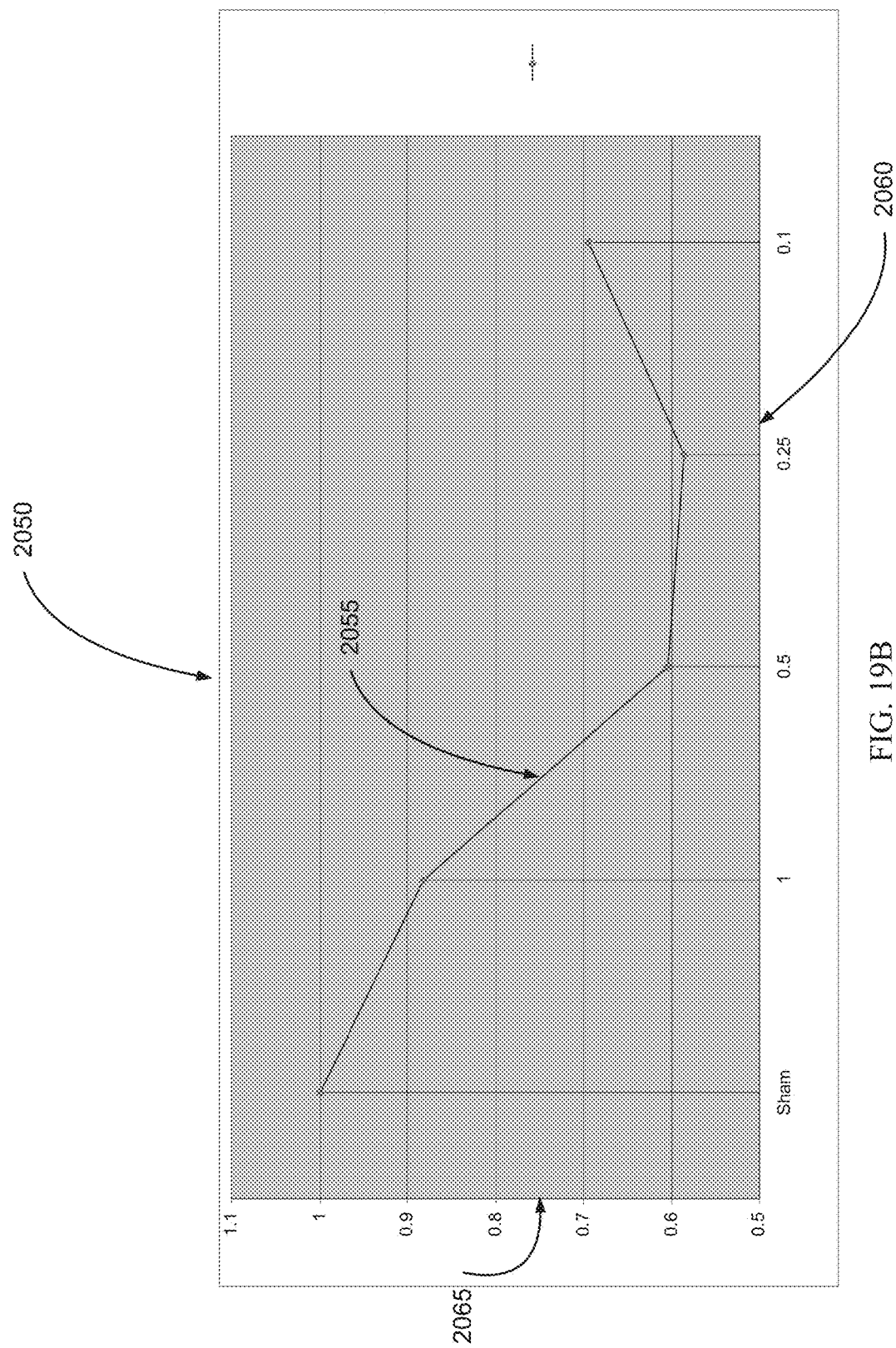

FIG. 1 schematically shows a photopill in accordance with an embodiment of the invention;

FIG. 2 schematically shows programming the photopill shown in FIG. 1, in accordance with an embodiment of the invention;

FIGS. 3A and 3B schematically show photopills similar to the photopill shown in FIG. 1 being used to treat diseased regions of a patient's GI tract, in accordance with an embodiment of the invention;

FIG. 4 schematically shows the photopills shown in FIGS. 3A and 3B contained in a package that turns on their internal electronic circuitry, which initiates clocks to time delay and exposure times when they are removed from the package, in accordance with an embodiment of the invention;

FIG. 5 schematically shows another photopill whose timer is turned on to time delay and exposure times when it is removed from a package in which it is contained, in accordance with an embodiment of the invention;

FIG. 6 schematically shows a photopill fitted with a controller and an antenna suitable for receiving a beacon signal;

FIG. 7 schematically shows the photopill shown in FIG. 6 being used to provide phototherapy to a diseased region of a patient's GI tract in accordance with an embodiment of the invention;

FIG. 8 schematically shows the photopill providing phototherapy to a diseased region responsive to directional beacon signals in accordance with an embodiment of the invention;

FIG. 9 schematically illustrates the very wide angle illumination pattern produced by a typical silicon phototherapy light source;

FIG. 10 schematically illustrates the effect of placing re-shaping optics in front of a typical silicon phototherapy light source;

FIG. 11 depicts a capsule device of the present invention fitted with a ring-shaped lens element in front of silicon light sources elements;

FIG. 12 illustrates another embodiment of the present invention, in which a small number of light sources are located on the end face of the capsule;

FIG. 13 shows the internal arrangement of the light source and associated optical elements in the embodiment depicted in FIG. 12;

FIG. 14 depicts an embodiment of the present invention in which initial triggering of the capsule is achieved by squeezing a metal ring;

FIG. 15 illustrates the general features of an optical movement sensing system that is used in certain embodiments of the present invention;

FIG. 16 provides further details of the optical movement sensing system depicted in FIG. 15;

FIG. 17 depicts a typical reflected light signal as detected by the photodetectors in the optical movement sensing system used in some preferred embodiments of the present invention;

FIG. 18 is a simplified flow chart illustration of a method for intraluminal phototherapy of the gastrointestinal (GI) tract, according to an embodiment of the invention;

FIG. 19A is a simplified dose-response graph depicting response of tissue to different doses of light;

FIG. 19B is an experimental dose-response graph depicting a response of mouse colon tissue to different doses of light according to an example embodiment of the invention; and FIGS. 20A-D are simplified diagrams of a length of a GI tract, and corresponding diagrams of examples of when light source(s) in a capsule are turned ON and OFF.

DESCRIPTION OF SPECIFIC EMBODIMENTS OF THE INVENTION

The present invention, in some embodiments thereof, relates to an ingestible phototherapy device which may be used for treating diseases of the gastrointestinal tract, and in particular, for treating inflammatory bowel disease (IBD).

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

A capsule which travels along the GI tract, and needs to provide therapeutic illumination to the GI tract, may require plenty of power to do so. A section below, titled "total treatment energy" describes how total battery power and a required therapeutic dose can limit the total area which may be treated.

In some embodiments of the invention, total battery power is not enough to power treatment of all the area which requires treatment. In some embodiments of the invention, only part of the GI tract is illuminated, a part which is known or assumed to be diseased. Sometimes even the diseased part is larger than an area which may be treated by one capsule. In some embodiments of the invention, one capsule illuminates part of a diseased area, and another capsule, swallowed later, illuminates another part of a diseased area. Certain disease conditions may require repeated procedures to achieve full or partial relief.

In some embodiments of the invention, only part of a diseased portion of the GI tract is treated, optionally providing an improvement in the disease. By way of a non-limiting example, treating only part of a lesion, reducing the lesion down to size.

It is useful to control when the illumination is turned on, and when turned off, based on when a capsule reaches a diseased area, and/or when the capsule reaches a specific part of the diseased area.

In some embodiments of the invention, measuring when a capsule reaches a diseased area is done by measuring time from an initial starting point. The starting point may be initiated when the capsule is removed from its package, or when a switch is pressed on the capsule, or when a sensor in the capsule senses something such as a pH change in its environment, a magnetic field applied to the capsule's environment, or a magnetic field weakening, and so on.

In some embodiments of the invention the capsule cycles illumination on and off. Such cycling provides many benefits, among which are: conservation of power; treating a larger area than possible in one stretch of illumination; limiting an illumination dose to an effective dose and no more; and in certain conditions, such as capsule speed and/or light intensity as described below, applying light in pulses may lead to better results than continuous illumination.

In some embodiments of the invention, the therapeutic illumination is provided at the same time as some other medical treatment such a taking a medicine to go along with the therapeutic illumination, optionally providing a synergism between the medicine and the therapeutic illumination.

A feature of some embodiments of the present invention is that all of the elements required for light irradiation in the GI tract, including bowel lesions, as well as means for controlling parameters associated with said irradiation, are located "onboard", that is, within the capsule device itself. As a result, the use of the capsule—and particularly self-use by the patient herself/himself—is facilitated by the fact that in some embodiments there is no requirement for the use of an additional apparatus, and/or an external apparatus and/or assistive personnel or medical professionals.

In some embodiments of the present invention some elements are external to the capsule device itself, such as external actuators for causing the capsule to turn lights ON or OFF, such as, by way of a non-limiting example an external magnet, vest, power transmitter, and/or a directional beacon for determining where in the GI tract the therapeutic light is to be turned ON.

Reference is now made to FIG. 1.

FIG. 1 schematically shows a cross section view of a photopill 20 providing phototherapy to a diseased portion of a wall 51 of a GI tract 50 of a patient, in accordance with an embodiment of the invention. A diseased portion of the GI wall 51 is indicated by a wavy portion 52 of the GI wall 51.

The photopill 20 comprises one, or optionally two, light sources 21 and 22 and light directors 31 and 32 housed inside a capsule housing 34 having an external wall 36 in accordance with an embodiment of the invention. Capsule housing 34 is characterized by dimensions suitable for swallowing and passage through the GI tract. By way of example, photopill 20 is optionally about 27 mm long and has a circular cross-section diameter of about 11 mm. Light sources 21 and 22, and light directors 31 and 32, are optionally located in a central portion of capsule housing 34 that is surrounded by a region, hereinafter referred to as "window", represented by a dashed portion 35 of wall 36 that is transparent to light provided by light sources 21 and 22. Light directors 31 and 32 receive light, represented by arrows 60, from light sources 21 and 22 respectively and direct the received light to pass through window 35 of wall 36 to illuminate annular regions, indicated by dashed lines 41 and 42 respectively, of GI tract 50. Regions 41 and 42, which are annular in the example embodiment of FIG. 1, define disc shaped volumes in which light from light sources 21 and 22 respectively are emitted. The photopill 20 comprises a power supply 24 and a controller 26, optionally located at opposite ends of a capsule housing 34. In an embodiment of the invention, the controller 26 comprises a timer 27 and controls light sources 21 and 22, as described below, responsive to clock signals provided by the timer.

It is noted that while phototherapeutic light is depicted in the drawings as being emitted annularly around an axis of the capsule, in some embodiments of the invention the phototherapeutic light is emitted from one or both ends of the capsule, and even both annularly and from ends of the capsule.

Light sources 21 and 22 may comprise any light source, such as a laser or LED, suitable for providing light in accordance with a desired phototherapy protocol for treating a diseased region of GI tract 50. By way of example, in the photopill 20, light sources 21 and 22 are shown as LEDs having light emitting junctions 29 and 28 located on an axis 37 of the capsule 20. In some embodiments of the invention light sources 21 and 22 provide light in substantially same wavelength bands. In other embodiments, light source 22 provides light in a wavelength band different from a wavelength band in which light source 21 provides light.

By way of example, diseased portion 52 of GI tract 50 is afflicted with, and photopill 20 is configured to provide phototherapy for, inflammatory bowel disease (IBD). To treat IBD in diseased portion 52 in accordance with an embodiment of the invention, light source 21 optionally provides light in a wavelength band having width of about ±30 nm centered at about 660 nm (nanometers) and light source 22 optionally provides light in a wavelength band of bandwidth about equal to ±30 nm centered at about 850 nm. Advantageously, intensity of light emitted by each light source 21 and 22 is such that between about 0.1 Joule to about 1 Joule of phototherapeutic light at each wavelength band is deposited per $cm^2$ of GI tract tissue afflicted with IBD. It is to be recognized that light sources emitting at other wavelengths in the visible spectrum (e.g. 440 nm) and near infrared (NIR) spectrum (e.g. 850 nm), or any combination thereof, may also be used to work the present invention.

It is noted that similar light intensities in NIR, red, and blue wavelengths have been tested to have substantially similar therapeutic effects, at least in a 1 Joule/$cm^2$ dose.

It is noted that emitting blue light requires more battery power to provide a similar light intensity.

It is noted that higher light dosage levels do not necessarily result in more efficient phototherapy of GI tract lesions. On the contrary, in many cases it has been found that lower dosage levels yield better treatment results than higher light irradiation levels. However, it is also to be recognized that a minimum effective dosage level also exists.

Consequently, an effective intestinal phototherapy capsule should be able to deliver a correct amount of treatment energy, which is within an effective dosage zone. A too-simple approach comprising swallowing a light source with a battery may not be effective and might even be harmful. Light dose control is therefore used, in order to avoid the following undesirable scenarios:

a) Under dosage will have no effect.

b) Over dosage will have no effect and might cause local damage, for example by heating the tissue.

c) The power source, such as a small battery, may be exhausted before an effective dose has been provided to the tissue, or to enough tissue area.

d) Coverage of the entire intestine wall's circumference may be required in order to obtain a satisfactory therapeutic approach.

It has been found that the light irradiation dose, commonly expressed in units of Joule per square centimeter, is affected by exposure time (seconds) and radiation power (Watts per square centimeter).

Some factors which influence dose delivery to the tissue include:

unevenness in illumination pattern projected on the intestine wall, thereby causing unevenness in the actual delivered dose;

changes in intestinal travel time, thereby causing changes in actual delivered dose due to change in exposure time.

Due to the size of a swallowable capsule and the power it may require to support the phototherapy throughout the intestinal travel, a silicon based phototherapy source is a highly practical solution used in some embodiments of the invention to solve the problem of meeting the aforementioned requirements. Such a silicon based source (for example HSDL-4400 manufactured by LIGHTON) has a very wide angle of illumination (typically 110-140 degrees) which forms an illumination pattern on the intestine wall which decays along the longitude axis (travel axis) of the capsule, as depicted in FIG. 9.

Reference is now made to FIG. 9.

In FIG. 9, a silicon phototherapy source 210 is depicted irradiating outwards towards the intestinal wall 212. Due to a wide angle of radiation 214 and due to the fact that radiation intensity is reduced, in some cases, in proportion to the square distance from the source, the radiation pattern absorbed by the intestinal wall 216 changes. At some points in the pattern, very high energy levels can be found (adjacent to the light source) while at other points, very low, sub-minimal threshold energy levels are found.

In some embodiments of the invention, using silicon phototherapy based source(s), the source optionally produces a known and measureable power level which can be compared against a required "dose response curve" to verify that the source(s) it delivers a correct amount of therapeutic energy to the tissue. In some embodiments of the invention, the dose response curve is programmed in the capsule, and the capsule calculates what amount of therapeutic energy has been delivered to the tissue, as is described in more detail below, with reference to a section titled "Total treatment energy".

In some embodiments of the invention, an off-the-shelf silicon emitter is used, optionally with a pre-manufactured optical lens and/or a reflector incorporated into the emitter, or alternatively, manufactured into the capsule's shell.

Although optionally narrowing the beam angle may prevent delivery of a sub-threshold and ineffective treatment dose to the intestine wall, narrowing may also create another problem, namely that of delivering insufficient therapeutic power to the entire intestine circumference in the region of the GI tract that is being treated.

As mentioned hereinbefore, a desired feature of some embodiments of the phototherapy intestinal capsule of the present invention is to deliver light therapy to the entire circumference of the intestinal segment being treated (i.e. 360 degree irradiation around the capsule). It may thus be seen that simply narrowing down the angle of the silicon illuminator will, in some instances, be impractical since an increased number of light sources which may be required to be placed around the external circumference of the capsule will not physically fit within the confines of a capsule which is small enough to be swallowed.

In some embodiments of the invention, a solution to this problem is provided by using beam-shaping optics which are designed to create a 360 degree irradiation coverage around the capsule's circumference, optionally also providing a narrow irradiation pattern along the capsule's longitudinal axis (travel axis). Such a beam may be formed with a specified width of its radiation pattern on the intestinal wall, providing power density and therefore, dosage delivery, in a more uniform and measurable form than without the beam shaping optics.

In some embodiments of this aspect of the invention, the silicon illuminators used, for example HIRTLB2-4G, manufactured by Huey Jann Electronics Co., have a wide radiation pattern, and are placed around the entire circumference of the capsule. Even 3 such illuminators can be used to obtain 360 degree coverage around the capsule's circumference. Re-shaping optics, shaped like a ring and placed over the light sources, concentrate the beam along its longitudinal axis into a narrower beam.

Reference is now additionally made to FIG. 10. As seen in FIG. 10 the irradiation beam 214a created on the intestinal wall using this embodiment is formed in the shape of a ring having a unified energy density 216a. This irradiation pattern is achieved by means of a convex lens 218 placed between light source 210 and intestinal wall 212. The direction of travel of the photopill capsule is indicated by arrow 220. Further details of this embodiment are provided in FIG. 11. Reference is now additionally made to FIG. 11, which shows a photopill capsule 230 fitted with a circumferentially arranged annular-shaped lens element 232 ("optical ring") overlaying silicon illumination sources 234.

Reference is now additionally made to FIG. 12. In an alternative preferred embodiment, instead of the illumination sources being arranged in a circumferential manner, they are disposed such that they point either in a forward or backward direction along the longitudinal axis of the device, as shown in FIG. 12. In this embodiment of the capsule device 240, fewer, but stronger, light sources 242 are needed in order to produce the required energy output. In order to achieve the desired illumination pattern on the intestinal wall, a funnel-shaped reflective optical element 244 is used to redirect the generated beam radially outward through an optically-transparent dome 246.

Reference is now additionally made to FIG. 13. The internal arrangement of this embodiment is illustrated in more detail in FIG. 13, in which the arrows 246 indicate the change in direction of the light beam generated by light source 242, when said beam is incident on the reflective element 244. In this way, the light beam is projected radially outward onto the internal wall of the GI tract 248.

The embodiments that have been discussed thus far achieve delivery of the desired dosage levels to the intestinal tissue by means of controlling the illumination pattern produced by the light sources. However, as mentioned hereinabove, it also possible to obtain the desired dosage levels by a different approach, namely by controlling the capsule's intestinal travel time, thereby causing changes in actual delivered dose due to change in exposure time.

While certain factors involved in exposure time, for example biological elements determining intestinal motility, are unable to be controlled, it is possible to control other factors. Thus, in one preferred embodiment of the present invention, the photopill device incorporates mechanisms for controlling the intensity of the emitted light in response to changes in the velocity of said device as it travels through the GI tract. These mechanisms will be described in further detail hereinbelow.

Another embodiment of the optical elements that may be used to generate the desired irradiation pattern is presented in FIG. 1, which shows light directors 31 and 32, which may be constructed of any suitable reflective material. In this embodiment of the invention, each light director 31 and 32 comprises a conical reflector 23 having an axis of rotation coincident with axis 37 of photopill 20. Relative locations of annular illuminated regions 41 and 42, whether the regions overlap or don't overlap, and if they overlap, by how much they overlap, are a function of spatial configuration of LEDs 21 and associated reflectors 23, a cone angle α of conical reflectors 31 and 32, and a diameter of a portion of GI tract 50 illuminated. For some configurations and GI tract diameters, and as shown in FIG. 1, annular illuminated regions 41 and 42 overlap over a relatively small area.

It is noted that light directors are not limited to simple conical light reflectors having a single cone angle, for which all surface elements make a same "inclination" angle with respect to an axis of the cone that is equal to a compliment of the cone angle. A conical light reflector may comprise a surface having regions that make different angles with respect to the cone axis. By way of example, a cone reflector in accordance with an embodiment of the invention optionally comprises surface regions having an inclination angle that gradually increases from about 30° to about 60° with distance of the surface region from the cone axis. Light directors are of course also not limited to cone reflectors or reflectors, and may for example, comprise any of various types of reflecting element, lenses, diffraction gratings, and/or light pipes and direct light from a single or a plurality of light sources to illuminate an annular region of a GI tract.

In one preferred embodiment of the invention, controller 26 turns on and turns off light source 21 and/or 22 responsive to clock signals provided by timer 27 so that photopill 20 provides phototherapy only to a region or regions of a patient's GI tract, for example diseased region 52 of GI tract 50, for which phototherapy is intended. Optionally, photopill controller 26 is programmable with at least one phototherapy start time and at least one phototherapy stop time to control when the controller turns on and turns off light source 21 and/or 22. A phototherapy start time is a time at which the controller turns on light source 21 and/or 22 to initiate phototherapy of a region of the patient's GI tract with light from light source 21 and/or 22, and a phototherapy stop time is a time at which it turns off light source 21 and/or 22 to terminate phototherapy provided by light source 21 and/or 22.

Phototherapy start and stop times are measured relative to a "clock-on" time, at which timer 27 begins clocking time to determine phototherapy start and stop times. Clock-on time is a time associated with a time at which the patient swallows photopill 20 to undergo phototherapy provided by the photopill.

Optionally, clock-on time is a time substantially equal to a time at which the patient activates a trigger, that is, with no delay. Optionally, clock-on time is a time substantially equal to a time at which the patient swallows photopill 20. In some embodiments of the invention, clock-on time is a time characterized by a predetermined time difference relative to a time at which a patient swallows the photopill. For example, clock-on time may be set after swallowing photopill 20 by a time it takes gastric acids to dissolve an insulator and close thereby a circuit that sets the clock-on time.

In some embodiments of the invention, clock-on time is determined by a change in an ambient environment of the photopill associated with using the photopill for phototherapy. The change causes setting of the clock-on time. For example, photopill 20 is optionally stored at a temperature less than body temperature. When swallowed, body heat raises the temperature of the photopill and the temperature change sets the clock-on time. In some embodiments, photopill 20 comprises a pH monitor, and clock-on time is set responsive to a change in pH, such as a possible change in pH detected when the photopill is swallowed by a patient and comes in contact with the patient's saliva. In some embodiments of the invention, the photopill comprises electrodes that are exposed to liquid or tissue in a patient's mouth or GI tract after the photopill is swallowed. Changes in direct current (DC) resistance or alternating current (AC) impedance between the electrodes are used to set clock-on times.

In some embodiments of the invention, clock-on time is a time at which the patient removes photopill 20 from a package in which it is contained. An act of removing the photopill from the package determines the clock-on time. Embodiments of the invention in which removal of photopill 20 from a package sets the clock-on time are discussed below with reference to FIG. 4 and FIG. 5. However, before beginning that discussion, a further embodiment of an activation mechanism will now be described with reference to FIG. 14.

Reference is now additionally made to FIG. 14, which illustrates a capsule device 310 fitted with an external metal ring 312. Immediately prior to use, the patient (or a medical attendant) squeezes said metal ring such that it is caused to make electrical contact with an annular metal plate 314 located interiorly to said ring. This circuit closure then connects the battery to the electronic circuitry within the capsule, thereby initiating its operation. In some embodiments of this type, an indicator light contained within the capsule, or on its surface, is illuminated in order to indicate that the capsule's circuitry has been activated.

Returning now to a more general discussion (with reference to FIGS. 4 and 5), a phototherapy start time is determined responsive to location of a diseased region in the GI tract of a patient who is to undergo phototherapy so that at least one of light source 21 and light source 22 is turned on at a time following clock-on time that it takes photopill 20 to travel through the GI tract to the diseased region. A phototherapy stop time associated with the phototherapy start time is optionally determined by an extent of the diseased region and a time it takes photopill 20 to travel through the diseased region so that light sources 21 and 22 are turned off after the photopill leaves the diseased region and is no longer in a position to illuminate the diseased region.

Location of a diseased region and its extent may be determined using any of various medical imaging modalities, such as capsule endoscopy, magnetic resonance imaging (MRI), X-ray computerized tomography (CT) and ultrasound imaging, or by simple patient indication, "it hurts here!", and/or professional palpation.

The travel time of photopill 20 may be estimated using data provided by various studies such "Compartmental Transit and Dispersion Model Analysis of Small Intestine Transit Flow in Humans", by Lawrence X. Yu, John R. Crison and Gordon L. Amidon; International Journal of Pharmaceutics, Vol. 40; 1999 and "Relationship of Gastric Emptying and Volume Changes After Solid Meal in Humans"; by Duane D. Burton, H. Jae Kim, Michael Camilleri, Debra A. Stephens, Brian P. Mullan, Michael K. O'Connor, and Nicholas J. Talley; Am J Physiol Gastrointest Liver Physiol 289, 2005. Optionally, travel times for a given patient are estimated from measurements of travel times of objects through the GI tract of the patient. For example, an acoustically reflective "calibration photopill" may be swallowed by the patient and progress of the calibration photopill through the patient's GI tract measured using ultrasound sensors or wireless transmission of an internal speed measurement to an external recorder.

As explained hereinabove, measurements of the movement of the photopill capsule may be used to calculate its average speed and location within the GI tract. In turn, these parameters may be used to control the start and stop times for the therapeutic illumination of the target tissue. In some embodiments of the present invention, both the determination of the photopill movements and the calculation of its speed and location from this determination, as well as control of the light source are performed by elements contained onboard, within the device itself, without additional externally-placed devices. In some embodiments of the invention, the device comprises an onboard accelerometer. Example uses of the onboard accelerometer include measuring the distance traveled along the GI tract, and optional measurement of orientation of the capsule. In these embodiments, phototherapy start and stop times are determined by onboard processing means (as will be described in more detail hereinbelow) using as their input the distance traveled by the photopill through the GI tract as determined from the accelerometer output and distance of the diseased region from a known location in the GI tract. Optionally, "travel distance" is determined by double integrating acceleration measurements provided by the accelerometer. For example, if the diseased region is located between 1.5 and 1.6 meters from the mouth, a phototherapy start time is a time at which the double integrated acceleration is equal to about 1.5 meters. A subsequent phototherapy stop time is a time at which the double integrated acceleration is equal to about 1.6 meters.

In some embodiments of the invention, capsule speed measurements are also used for stopping the illumination. The stopping prevents an overdose of an area where the capsule has stopped, and also prevents wasting power.

Reference is now additionally made to FIG. 15. In other embodiments, the onboard means for determining and measuring the movements of the photopill comprise optical motion sensing means (similar, in principle to an optical mouse of the type commonly used to position a cursor on a computer screen). In these embodiments, as depicted in FIG. 15, the capsule 320 includes an optical movement sensing element which comprises an illumination source ("illuminator") 322, directed outwards through the side of the capsule by way of its transparent shell, and two or more optical photodetectors 324 also directed to a point outside the capsule which are responsive to optical signals reflected back from the intestinal walls 326.

The illuminator, such as the SMD LED by SunLED model XZMDKT53W-6, as can be found at www.sunledusa.com/products/spec/XZMDKT53W-6.pdf, is placed in a way which directs its light onto the small intestine wall to the same location that the photo detectors are focused on. A pair of photo detectors (such as the SMD HSDL-54xx series of PIN photodetectors by LiteON) are placed in a way that they are both focused to the same distance away from the capsule but each is placed in pre-defined distance (such as 5 mm) from the other, along the longitude axis of the capsule.

In some embodiments of the invention, the therapy illumination light sources provide the light which is reflected onto optical motion sensors. Such embodiments are useful in specific cases, such as when light therapy is turned ON by a mechanism other than optical motion sensing, such as a pH sensor, and/or a timer. Such embodiments are also useful in specific cases, such as when light therapy is provided along the entire GI tract.

Reference is now additionally made to FIG. 16. In an embodiment depicted in FIG. 16, when the optical elements are positioned as described above, while the capsule is moving along the small intestine 336, the light emitted by the illuminator 346 (via transparent shell 335) and reflected back from the small intestine wall, is detected by the detectors 344 and 345. The field of view of detector 345 on the intestinal wall is indicated by numeral 350. Since the detectors are located in a pre-defined distance 338 from each other, a slightly different reflection will be obtained by the two detectors. As the capsule progresses (in the direction indicated by arrow 348), the detected signals will differ in phase to a degree which is dependent on the speed of capsule movement. FIG. 16 also shows the output of photodetectors 344 and 345 when the capsule is moving within the intestine. Reflections from the intestine wall (such as A and B) are detected by the photo-detectors according to the direction of movement. In the example demonstrated in this figure, the reflection A and then B will first be detected by the detector located closest to the leading edge of the capsule (i.e. detector 344).

Reference is now additionally made to FIG. 17. The output of the pair of detectors is also graphically illustrated in FIG. 17. As may be seen from this figure, the detection by the leading detector 344 occurs earlier than the detection by detector 345 that is located closer to the trailing edge of the device.

It may thus be appreciated that once the identity of the first detector that detects a reflected signal is known, the direction of movement can be obtained. Also, since the detectors are placed in a pre-defined distance from each other, the speed of movement can be obtained by calculating the time elapsed between detection of a specific event by detector #1 and the detection of the same event by detector #2 and dividing the distance between the detectors by the detection difference time.

The values of movement direction and speed can be obtained by several methods, such as phase detector or by software techniques such as cross correlation between the two detectors outputs.

Following the determination of the speed and direction of movement of the device, its location within the intestine can be determined by integrating the speed over time.

The photopill 20 may be programmed with phototherapy start and stop times to provide phototherapy to a diseased region of a patient's GI tract optionally using a personal computer (PC).

Reference is now additionally made to FIG. 2. By way of example, FIG. 2 schematically shows a medical professional 69 programming photopill 20 using a PC 70 having a monitor 71, in accordance with an embodiment of the invention. PC 70 is connected by a wire or wireless communication channel with a docking station 72 in which the photopill is seated for programming. Docking station 72 optionally communicates with photopill 20 to transmit commands from PC 70 to the photopill. In some embodiments of the invention the following communications are used: light (optionally intensity modulated); radio frequency (RF); and wired communications by physical contact.

In an embodiment of the invention, the medical professional displays an image 74 of the patient's GI tract 50 on the PC's monitor 71 with the diseased region or regions highlighted or otherwise indicated. By way of example, in image 74, a diseased region 52 of the patient's GI tract 50 is schematically highlighted by shading. The medical professional selects a region of GI tract 50 to be illuminated with phototherapeutic light from photopill 20 by selecting an image of the region in image 74. Selection of a region in image 74 may be done using any of various methods known in the art such as by using a mouse to highlight the region or surround it with a border, or if monitor 71 is a touch screen, by touching the region to be selected. In FIG. 2, by way of example, the medical professional uses a mouse 73 to draw an ellipse 55 to define a region that includes diseased region 52 for receiving phototherapy.

PC 70 optionally computes phototherapy start and stop times responsive to the location of the indicated region and patient data relevant to speed with which photopill 20 is expected to travel through the patient's GI tract 50. The calculated phototherapy start and stop times are communicated from PC 70 to docking station 72, which transmits programming signals to photopill 20 to program the photopill with the start and stop times.

For an embodiment of the photopill 20 which includes an accelerometer, or optical motion sensing, which provides data for determining distance in the GI tract traveled by the photopill 20, the PC 70 is optionally used to program the controller 26 to turn on and turn off light source 21 and/or light source 22 when distances traveled by the photopill determined from accelerometer output are equal to distances along the GI tract that bracket diseased region 52. Optionally, the distances that bracket the diseased region are locations at which ellipse 55 crosses a region of the GI tract enclosing the diseased region.

For a photopill comprising a pH monitor, in accordance with an embodiment of the invention, the photopill is optionally controlled responsive to pH in the GI tract. It is known that different portions of the GI tract are characterized by different pH values, and the photopill is programmed to turn on and provide phototherapy to a diseased region of the GI tract at a start time at which it reaches a region of the GI tract having a pH value characteristic of a portion of the GI tract in which a diseased region is located.

In some embodiments of the invention, the medical professional 69 optionally programs the photopill 20 with a desired intensity, and/or wavelength of phototherapeutic light to be applied to diseased region 52 optionally in addition to, or even instead of, programming the photopill 20 with phototherapy start and stop times. For example, in embodiments of the invention for which light source 21 and 22 are tunable, or for which light source 21 provides therapeutic light in a wavelength band different form that of light source 22, the medical professional can also program photopill 20 to deliver different combinations of wavelengths of therapeutic light to diseased region 52. In some embodiments of the invention, the medical professional determines intensity of light provided by light sources 21 and 22 responsive to a total desired amount of therapeutic light to be deposited in diseased region 52.

As discussed hereinabove, the photopill capsule of the present invention may be programmed in order to control the activation and deactivation of the therapeutic light source, thereby ensuring that therapeutic light irradiation occurs at the desired site within the GI tract, as well as preventing unnecessary irradiation of non-target sites and premature depletion of the capsule battery.

In order to implement the programmable functionality, the capsule may, in one embodiment, comprise a programmable microprocessor controller which is small in size, low in current consumption, does not require external components to be operated and can function within the wide range of operating voltage supplied by the capsule's battery.

One preferred example of a microprocessor suitable for this task is MicroChip's PIC12F1822 processor, which is a self contained re-programmable controller, of a small size (3×3 mm), and requiring no external components for its operation. This microprocessor can operate at voltages ranging from 1.8V to 5V. The PIC12F1822 has very low power consumption and contains digital inputs/outputs as well as several analog inputs for sampling and signal processing.

As discussed hereinabove, the photopill capsule may be used in one or more of several different activation/deactivation modes:

a) Timer based activation/deactivation;
b) Location based activation/deactivation;
c) pH based activation/deactivation;
d) temperature-change based activation/deactivation;
e) moisture and/or humidity based activation/deactivation; and
f) external magnet based activation/deactivation.

It is noted that the different modes of activation/deactivation can optionally be used in combination, by using more than one as a base for activation/deactivation.

Timer Based Activation

Some embodiments of the inventions are designed to be simple, suitable for home use, without presence of medical practitioners. A patient optionally activates a capsule before swallowing. The activation starts operation of the capsule, be it time measurement, or pH measurement. The patient swallows the capsule, and the capsule may turn light sources on at a predetermined time after activation, and/or after sensing a specific pH and/or moisture and/or temperature change.

In some embodiments of the invention, the patient self administers, that is swallows, several capsules, optionally swallowing a new capsule after an old capsule has exited the body, and/or a day later, and/or a different amount of time. The several capsules may each include pre-programming of a controller to start phototherapeutic illumination after a different time period from activation or from pH sensing, such that each of the several capsules may illuminate a different section of the GI tract. Optionally, the different capsules may be marked as to which capsule starts illuminating after what time, and/or marked so as to identify in what order to swallow the capsules. Such marking may be by color-coding, and/or by printing times on the capsules and/or on the packages. Optionally the different capsules may be pre-programmed for controlling different start times during manufacture, and marked according to their start times. Optionally the different capsules may be pre-programmed for controlling different start times by a medical practitioner who provides the capsules to a patient.

In some embodiments of the invention, several capsules, optionally with different time lags before illumination, are packaged as a kit.

This mode of operation will mostly be used for conditions where relatively predictable intestine travel speeds prevail, such as in clinical studies where patients are selected carefully according to pre-defined profiles, and are using the capsule in well controlled and monitored environment.

The capsule is triggered once it is removed from its package or by the patient before swallowing. Once triggered, the internal processor counts the time elapsed from trigger and once the pre-defined time-delay value is reached the capsule is activated (i.e. the therapeutic light source is turned on).

The pre-defined delay value reflects stomach delay time (for example—half an hour in a controlled environment) and additional delays to allow the capsule to reach its treatment target area (for example—for a 3 hour intestinal travel time, a 2 hour delay is required to reach the terminal ileum area).

Location Based Activation

This mode is suitable, by way of some non-limiting examples, for use in cases where no prediction of intestine travel time exists, and/or where large variations are expected in travel speed values, and/or in scenarios where location based activation is readily available, such as in some clinics.

In order to use location based activation, it is possible to use one or more of the mechanisms for determining the position and progress of the capsule within the GI tract, such as the accelerometer and optical position sensing means, described hereinabove. Using these mechanisms, it is possible to measure the progress of the capsule within the small intestine and to provide a momentary average travel speed, which if integrated, produces the distance traveled.

By knowing the distance traveled, the capsule can now be set to be activated at an absolute location within the small intestine (such as—4.5 meters beyond the pyloric sphincter) regardless of the time it takes to get there. It should be noted that this method is not particularly accurate, due to variable delays in stomach transit and also due to measurement errors.

It is noted that in embodiments using optical speed sensing, it is possible to detect when a capsule enters the small intestine, because in the stomach, the capsule is not in constant contact with tissue as it is in the small intestine. Once a valid and/or constant speed measurement from the optical sensor is obtained—it indicates, for example, that the capsule has entered the small intestine.

Another method for determining location is proximity to a belt and/or patch placed on a patient's body next to a location where the capsule is to be activated. The proximity may be detected by having an RFID tag within the capsule, and an RFID detector on the belt and/or patch. The RFID detector may cause activation of the capsule by activating a switch in the capsule. The switch may be, by way of a non-limiting example, a magnetic switch, and the activation by activation of an electromagnetic coil.

Another method for determining location is imaging using standard medical imaging. When the capsule is determined to be at a desired location the capsule may be activated remotely, as described above.

In some embodiments of the invention, location of a diseased region and its extent is by patient indication, the patient indicating where it hurts, and/or professional palpation. The capsule is located in the patient by a coil, such as used in metal detector, detecting and displaying a proximity of the capsule to the coil, at which time a signal is sent to the capsule to turn therapeutic illumination ON. The signal is optionally an electromagnetic signal provided by the coil which is used to detect proximity of the capsule. In some embodiments of the invention, a magnet is inserted within the capsule, in order to produce a more pronounced signal for detection by the coil.

pH Based Activation

Since pH values change significantly along the GI tract, the location of the capsule can be obtained by means of measuring the pH in the region in which the capsule is currently located. The following table provides minimum and maximum pH values typically found in the various regions of the GI tract in human subjects:

| Location | Min pH | Max pH |
| --- | --- | --- |
| Stomach | 1.0 | 2.5 |
| Proximal small Intestine | 6.1 | 7.1 |

-continued

| Location | Min pH | Max pH |
| --- | --- | --- |
| Terminal ileum | 7.1 | 7.9 |
| Caecum | 6.0 | 6.8 |
| Left Colon | 6.3 | 7.7 |

It may thus be appreciated that the ambient pH value can be used to identify the entry of the capsule into the small intestine. From that point onwards, other mechanisms (such as the accelerometer and optical motion sensor described hereinabove) can be employed in order to measure the change in location within the small intestine.

Measurement of pH can be performed using a pH sensor incorporated within the capsule. While any suitable sensor can be used, in one embodiment, the pH sensor may be an ISFET (ion sensitive field effect transistor) sensor, such as the sensor used in a telemetry capsule described in US 2004/0106849.

Programming a Capsule

In some embodiments of the present invention, an onboard microprocessor is also used for purposes other than activation/deactivation of the therapeutic light source, including (but not limited to) control of light source output intensity and calculation of speed and location parameters.

Setting of the programmable parameters in the capsule can be achieved, for example, by:

i) Pre-defined settings during manufacture of the capsule.
ii) Programming by a physician prior to use.

Manufacturing setup is a method whereby operating values are programmed into the capsule during the capsule manufacturing process. In particular, in some embodiments of the invention, several versions of the microprocessor's software are prepared in advanced, each containing different setup (for example—one version might include operation delayed by 0.5 hour while another might include operation delayed by 2 hours).

The microprocessors are programmed with the different software versions and are assembled into capsules which are now labeled in order to distinguish between the different versions.

A second approach involves re-programming the capsule prior to ingestion. Thus, in cases where special setup parameters are needed, for example if the patient's small intestinal travel speed is unusually high or low, the physician can change the setup parameters of the capsule in order to take the unusual physiological parameters into account. The re-programming can be achieved by means of 2-way wireless communication with the capsule, where parameters can be read from the capsule and written back into the capsule.

Such wireless communication can be achieved using standard wireless protocols such as WiFi or Bluetooth, or alternatively, by means of optical transmission between a physician's computer and the capsule.

By way of a non-limiting example, the following are references which describe methods by which a medical practitioner can find out intestine travel speed:

Breath test (lactose-ureide breath test): www.eurostarch.org/Priebe.pdf;

Wireless smart pill: www.touchbriefings.com/pdf/2602/Smartpillcorpfinal_tech.pdf;

Pillcam image processing: www.ima.org.il/imaj/ar04sep-3.pdf; and

Radio telemetry: www.springerlink.com/content/t038j55020247w75.

Stop Time

In some embodiments of the invention, the photopill is pre-programmed with a lights-off time, or stop time.

In some embodiments of the invention, the photopill is optionally de-activated in response to changes in pH and/or detected position within the GI tract.

In some embodiments of the invention, the photopill is not programmed with a stop time. Instead, the photopill, once its light source is turned on, continues to generate phototherapeutic light until its power source no longer has sufficient energy to power the light source.

In some embodiments of the invention, the photopill is programmed to turn lights off based, at least in part, on the photopill's speed, as measured by an accelerometer.

In some embodiments of the invention, the photopill is programmed to turn lights off based, at least in part, on the photopill's speed, as measured by an optical speed sensor.

In some embodiments of the invention, the photopill is programmed to turn lights off based, at least in part, on the photopill's location, as calculated by an accelerometer.

In some embodiments of the invention, the photopill is programmed to turn lights off based, at least in part, on the photopill's location, as calculated by an optical speed sensor.

Reference is now additionally made to FIGS. 3A and 3B. FIGS. 3A and 3B schematically illustrate photopills 121 and 122 being used to apply phototherapy, in accordance with an embodiment of the invention, to a GI tract 50 of a patient afflicted with inflammatory bowel disease (IBD) in regions 52A and 52B of the tract. Photopills 121 and 122 can be similar to photopill 20 shown in FIG. 1 and comprise light sources 21 and 22 (FIG. 1) configured to emit light optionally in wavelength bands centered at 440 nm, 660 nm, and 850 nm, having bandwidths of about 30 nm. In FIG. 3A photopill 20 is swallowed at or about a clock-on time to of its timer 27 (FIG. 1) and begins traversing the patient's GI tract 50. The photopill is programmed, optionally as shown in FIG. 2, to turn on both light sources 21 and 22 at a phototherapy start time t1 following to at which it is estimated it will reach diseased region 52A and to maintain the light sources on until a phototherapy stop time t2 at which it leaves the region.

The photopill 121 is shown at various locations along GI tract 50 as it traverses the tract, and estimated locations of photopill 121 at times to, t1, and t2 are labeled with the times. The photopill's window 35 (FIG. 1), through which therapeutic light from light sources 21 and 22 is transmitted to illuminate regions of the tract, is shown unshaded to indicate when light sources 21 and 22 are off and is shown shaded to indicate when the light sources are on. In diseased region 52A, light sources 21 and 22 are on, and window 35 is shown shaded. In accordance with an embodiment of the invention, photopill 121 is programmed to deliver a total amount of therapeutic optical energy to diseased region 52A in each of the wavelength bands centered at 440 nm, 660 nm, and 850 nm equal to about 0.1-1 Joules/cm2. To provide the desired energy deposition, photopill 121 illuminates diseased region 52A with intensity of light in each band equal to the desired energy deposition divided by a time that the photopill is in the vicinity of, and illuminating the diseased region.

By way of example, assume power supply 24 of photopill 121 does not have enough energy to provide therapeutic light to both diseased regions 52A and 52B, and the photopill is used to provide phototherapy only to diseased region 52A. Photopill 122, schematically shown in FIG. 3B is used to deliver phototherapy to diseased region 52B. Photopill 122 is swallowed at or about a clock-on time $t_o$* and is programmed to turn on its light sources 21 and 22 at a time t3 following $t_o$*, at which time t3 photopill 122 is expected to arrive in the vicinity of diseased region 52B. Photopill is programmed to maintain its light sources on after turning them on at time t3 until a time t4 when the photopill is expected to leave the vicinity of diseased region 52B. In FIG. 3B, photopill 20 is shown passing through diseased region 52A with its light sources off (window 35 clear) and with its light sources 21 and 22 (window 35 shaded) on in the vicinity of diseased region 52B.

Reference is now additionally made to FIG. 4. In an embodiment of the invention, photopills 121 and 122 are packaged in a protective package 130 schematically shown in FIG. 4 after they have been programmed with their respective phototherapy start and stop times and removal of a photopill from the package sets the clock-on time of the photopill.

Optionally, package 130 is formed having sockets 132 into which photopills 121 or 122 are inserted and stably held. In accordance with an embodiment of the invention, controller 26 comprised in photopills 121 and 122 has a magnetically activated "clock-on switch" (not shown) that operates to set the clock-on time in the photopills and package 130 comprises magnets 134 that generate a magnetic field in the vicinity of each socket 132. After a photopill 121 or 122 is programmed, when it is first placed in a photopill socket 132 of package 130, the magnetic field generated by magnets 134 in the vicinity of the socket arms the magnetic clock-on switch in the photopill's controller 26. When the photopill is removed from its socket and distanced from the magnetic field in the socket, the magnetic field in the vicinity of the photopill decreases substantially. The decrease in the magnetic field activates the magnetic clock-on switch to set a clock-on time for the photopill.

In some embodiments of the invention, a photopill comprises a clock-on switch, which is mechanically operated to set a clock-on time for the photopill when it is removed from a package.

Reference is now additionally made to FIG. 5. FIG. 5 schematically shows a photopill 150 seated in a socket 160 of a package 162, which mechanically operates a clock-on switch in the photopill to set a clock-on time for the photopill when it is removed from the socket. Photopill 150 optionally has an elastic wall region 152, shown shaded and hereinafter referred to as a "push-button 152", which is depressed and subsequently released to operate the switch. Socket 160 is formed having a protuberance, referred to as a spur 161, which is configured to depress push-button 152 when photopill 150 is seated in the socket. After photopill 150 is programmed with phototherapy start and stop times, the photopill is seated in socket 160 so that spur 161 depresses push-button 152. Depressing the push-button arms the clock-on switch. When photopill 150 is removed from socket 160 push-button 152 is released and the clock-on switch is switched to set the clock-on time for photopill 150.

It is noted that photopills are not limited to having their clock-on times set by a magnetic field or mechanically. In some embodiments of the invention a photopill clock-on time is set by exposure of the photopill to light. Optionally, the photopill comprises a light sensor that generates a signal responsive to incident light. The photopill is packaged in a light-tight sleeve or package. When removed and exposed to light, the light sensor generates a signal that causes the clock-on time to be set.

In some embodiments of the invention, a photopill is activated to provide phototherapy to a region of a patient's GI tract responsive to a signal, hereinafter a beacon signal, transmitted by a beacon transmitter external to the patient's body, optionally mounted on the patient's body.

Reference is now additionally made to FIG. 6. Optionally FIG. 6 schematically shows a photopill 170 comprising a controller 172 having a receiver, represented by an antenna 174, for receiving a beacon signal. Optionally, photopill 170 comprises a configuration of light sources for emitting phototherapeutic light different from that comprised in photopill 170 shown in FIG. 1. Photopill 170 optionally comprises a plurality of light sources 176 symmetrically positioned along a circumference of a circle to directly illuminate an annular region of a region of a GI tract in which it is located, optionally through a window 35 of the photopill.

Optionally, controller 172 is configured to process a proximity beacon signal established or transmitted by a proximity beacon located on the body of a patient whose GI tract is to be treated by photopill 170 with phototherapy. The controller activates the light sources 176, that is, turns the light sources 176 on and off, as the photopill traverses the patient's GI tract, responsive to a signal received by antenna 174 from the proximity beacon that indicates that the photopill is in a near neighborhood of the transmitter and therefore located in a region of the GI tract intended to receive phototherapy.

Any of various types of signals may be suitable as a proximity beacon signal. For example, a proximity beacon, in accordance with an embodiment of the invention, may provide an ultrasound or radio frequency (RF) proximity beacon signal. In some embodiments of the invention, a proximity beacon generates a relatively constant field such as a magnetic field inside the patient's body. Controller 172 senses the field and determines when to turn on light sources 176 responsive to the strength of the sensed field.

Reference is now additionally made to FIG. 7. FIG. 7 schematically shows photopill 170 being used to provide phototherapy to a diseased region 52 of a patient's GI tract 50 responsive to beacon signals represented by dashed concentric circles 180, hereinafter referred to also as "signal circles", transmitted by a beacon 182 located external to the patient's body, close to the diseased region. Intensity of beacon signals 180 decreases with distance from beacon 182. Photopill 170 is optionally programmed to turn on light sources 176 and maintain the light sources on as long as intensity of beacon signals 180 that receiver 174 receives is greater than a predetermined threshold intensity. A region in the patient's body at which beacon signal intensity is about equal to or greater than the predetermined signal strength is schematically indicated by an area within a solid "threshold circle" 180* concentric with "signal circles" 180.

In FIG. 7 photopill 170 is shown at various locations in GI tract 50 after it is swallowed by the patient. The photopill remains off (that is light sources 176 are off), as indicted by clear window 35 as long as it remains outside of threshold circle 180*. Once it reaches threshold circle 180* and remains within a region of the patient's body under the circle's area, beacon signals 180 that photopill 170 receives have intensity greater than the predetermined threshold intensity and the photopill is "on" and delivers therapeutic light to diseased region 52 of GI tract 50. The on state of photopill 170 within circle 180* is indicated by shading of its window 35.

In some embodiments of the invention, a photopill similar to photopill 170 processes directional beacon signals transmitted by a directional beacon to determine locations of the photopill in a patients GI tract and determine when to turn on its light sources and provide phototherapy to the GI tract.

In some embodiments of the invention, the beacon marks a "turn on" location for the capsule, such that the location is optionally where the beacon signal strength decreases after the strength increased while the capsule neared the beacon.

Reference is now additionally made to FIG. 8. FIG. 8 schematically shows a photopill 180 providing phototherapy to a diseased region 52 of a patient's GI tract 50 responsive to directional beacon signals that the photopill receives from a directional beacon 200 mounted at a known location external to the patient's body. By way of example, directional beacon 200 is shown close to the patient's body in a region of the navel.

Directional beacon 200 transmits a rotating beam, represented by a block arrow 202 of optionally acoustic energy, whose frequency "f" and intensity "I" change respectively with an angular direction "φ" along which the beam is transmitted and a radial distance "r" in the patient's body from the beacon. Angular direction φ of beam 202 is an azimuth angle about an axis (not shown) that passes through beacon 200 and is perpendicular to the coronal plane of the patient's body (an axis perpendicular to the page of FIG. 8). Direction of rotation is optionally clockwise and indicated by a curved arrow 204. Frequency f and intensity I are written $f(\varphi)$ and $I(r)$ to explicitly show their respective dependence on azimuth angle and radial distance relative to directional beacon 200.

A location of a region in the patient's body may be determined relative to the position of directional beacon 200 by determining a frequency and intensity of beam 202 at the location. For example, a lookup table may be used to map a frequency $f(\varphi)$ and intensity $I(r)$ of beam 202 measured at a given location in a patient's body to the azimuth angle φ and radial distance r coordinates of the location. In FIG. 8, diseased region 52 is schematically shown located between azimuth angles $\varphi_1$ and $\varphi_2$ and radial distances $R_1$ and $R_2$ relative to directional beacon 200. In the figure, dashed lines labeled respectively $\varphi_1$ and $\varphi_2$ bracket the angular extent of diseased region 52 and dashed lines labeled $R_1$ and $R_2$ respectively bracket the radial extent of the diseased region. In an embodiment of the invention, the diseased region is associated with corresponding frequencies in a range of frequencies between frequency $f(\varphi_1)$ and frequency $f(\varphi_2)$ and corresponding intensities between $I(R_1)$ and $I(R_2)$.

After photopill 170 is swallowed and travels along GI tract 50 its receiver 174 (FIG. 6) receives directional beacon signals 202 transmitted by directional beacon 200, which signals are processed by controller 172 to determine their frequency and intensity. Upon receiving directional signals having frequency and intensity in the ranges $f(\varphi_1)$-$f(\varphi_2)$ and $I(R_1)$-$I(R_2)$ that mark the location of diseased region 52, the controller turns on light sources 176 to illuminate the diseased region with phototherapeutic light.

It is noted that whereas in the above description a photopill provides light to a diseased region of the GI tract, a photopill in accordance with an embodiment of the invention is not limited to providing phototherapy to a diseased region of the GI tract. A photopill may for example be used to illuminate a portion, or substantially all of a patient's GI tract, to provide preventive therapy to a patient.

In some embodiments of the invention, a patient is treated by a photopill in a clinical setting. The clinical setting may concentrate treating several patients at the same time. The photopills may optionally be tracked in the patient's body using a medical imaging system, and a medical practitioner may optionally decide when to turn on or off therapeutic illumination based on results of the medical imaging. The medical practitioner may optionally decide when to turn on a timer within the photopill based on results of the medical imaging.

Embodiments of the photopill capsules of the present invention may be used by a patient to treat conditions in the gastrointestinal tract in the following manner:

The photopill capsule may be self-administered by the patient after waking up in the morning, at least half an hour before eating. Alternatively, it may be taken at least 4 hours following food consumption (clear fluids may optionally be consumed at any time). This requirement ensures that the stomach is empty and remains empty of optical obstruction until the capsule travels away from the stomach into the small intestine.

The photopill capsule may be packed in a 6 or 10 capsule package. Before usage, the user removes the capsule from its package.

Once removed from its package, the capsule may be activated (by means of one of the activation modes described hereinabove, and optionally indicated by a visible red light flashing once a second, 3 times, from within the capsule) and should be swallowed within 5 minutes of removal from package. The user should verify that the capsule is active. In another version of the capsule, activation may be achieved by squeezing the capsule (as described above). In this context, activation of the capsule refers to the activation of a timer, thereby placing the capsule in a state in which it is ready to be swallowed by the patient. It should be noted that the therapeutic light source will be turned on later, in response to signals generated by the timer, accelerometer or optical detector.

Reference is now additionally made to FIG. 18, which is a simplified flow chart illustration of a method for intraluminal phototherapy of the gastrointestinal (GI) tract, according to an embodiment of the invention.

FIG. 18 depicts a method which includes:

swallowing a capsule comprising one or more light sources capable of emitting light at wavelengths and intensities suitable for providing a phototherapeutic effect (1810); and activating the light sources when the capsule is in the gastrointestinal tract.

Estimation of Radiation Dose for Optimal Performance

An element in effective phototherapy is a determination of a radiating protocol for optimal performance.

Selection of optimal radiation required for phototherapy is a field known as Low Level Light Therapy (LLLT). A radiation regime known in LLLT is expressed by the Ardnt-Schulz curve, also referred to as the biphasic dose response curve.

Reference is now made to FIG. 19A, which is a simplified dose-response graph 2000 depicting response of tissue to different doses of light. FIG. 19A depicts an Ardnt-Schulz curve 2030, using a qualitative X-axis 2010 of increasing illumination dose, and a qualitative Y-axis 2020 of response to the light dose. The Ardnt-Schulz curve 2030 shows that the response to an increasing radiation dose starts from no response to a low dose, increases with increasing dose, then decreases with increasing dose.

The biphasic dose response means that low levels of light have a much better effect on stimulating and repairing tissue than higher levels of light. In fact, there is an optimum of best response where lower light levels or higher light levels yield much less effective treatment.

Experimental Results

Our experiments show which specific dose has an optimal effect on acute DSS colitis in mice, which is taken to provide a good indication for doses in humans.

Reference is now made to FIG. 19B, which is an experimental dose-response graph depicting a response of mouse colon tissue to different doses of light according to an example embodiment of the invention. FIG. 19B depicts a response curve 2055, an X-axis 2060 of illumination dose in Joules/cm$^2$, and a normalized Y-axis 2065 of response to the light dose. The Y-axis is normalized such that untreated colitis in mice, which received a sham treatment that included inserting a capsule but not operating the therapeutic light source, is taken to have a value of 1, and lower levels of colitis are seen in treated mice. The X-axis depicts dosages of 1 Joule/cm$^2$; 0.5 Joule/cm$^2$; 0.25 Joule/cm$^2$; and 0.1 Joule/cm$^2$.

The response curve 2055 shows that the response to illumination dose is optimal at 0.25 Joule/cm$^2$, and is good in a broader range starting from 0.1 Joule/cm$^2$, and extending up to between 0.5 Joule/cm$^2$ and 1 Joule/cm$^2$.

In a publication in Dose Response Society 2009, which may be found at www.ncbi.nlm.nih.gov/pmc/articles/PMC2790317/pdf/drp-07-358.pdf it is stated that if insufficient energy is applied, there will be no response (because a minimum threshold has not been met); if more energy is applied a threshold is crossed and bio stimulation is achieved; and when too much energy is applied then the stimulation disappears and is replaced by bio-inhibition instead.

It is accepted to approach the LLLT field with two main irradiation parameters—"medicine" and "dose". The "medicine" is considered to be comprised of several elements, of which the important ones are wavelength (typically measured in nm) and irradiance (typically measured in W/cm2). The "dose" is considered to include additional elements, for example energy density (J/cm2) and irradiation time (s).

Researchers have investigated the above parameters for different pathologies, trying to determine an optimum treatment protocol for each. The irradiation area most used was 1 mW to 500 mW of LED or low power laser irradiation.

Some example protocol testing publications include:
Phototherapy Doses in Humans:

| Application | Dominant Wavelength | Power | Energy density | Comments |
|---|---|---|---|---|
| Oral Mucositis | 660 | 40 mW | 4 J/cm$^2$ | |
| Oral Mucositis | 660 | 50 mW | 4 J/cm$^2$ | |
| Oral Mucositis | 830 | 100 mW | 4 J/cm$^2$ | Pediatric Mucositis |
| Oral Mucositis | 630 | 30 mW | 5 J/cm$^2$ | Pediatric Mucositis |
| Oral Mucositis | 670 | | 4 J/cm$^2$ | Pediatric Mucositis external 14 daily treatments |
| Oral Mucositis | 645 | 7.8 mW | 0.99 J/cm$^2$ | 21 sessions, 3 times a day for one week, 300 seconds each exposure |
| Oral Mucositis | 880 | 74 mW | 3.6 J/cm$^2$ | 5 sessions, 30 seconds each |
| Oral Mucositis | 660 | 40 mW | 2.4 j/cm2 | 5 × 2.4 j/cm2 per point, 14.4 j/cm2 per session, contact mode |
| Nasal Mucosa | 780 | 70 mW | 2.1 j/cm2 | 3 × 2.1 j/cm2 per point, 6.3 j/cm2 per session, contact mode |
| Gingivitis | 670 | 1.4 mW | 0.34 J/cm$^2$ | Single session of 30 seconds |
| Gingivitis | 632 | | 1.2 J/cm$^2$ | |
| Oral Mucositis | 640 | | 4.5 J/cm$^2$ | Pediatric Mucositis 4-7 days, 40 seconds each area |
| Gingival Fibroblast | | | 3.37 J/cm$^2$ | |
| Oral Mucositis | 630 | 60 mW | 2 J/cm$^2$ | |
| Oral Mucositis | 830 | 250 mW | 35 J/cm$^2$ | 5 days |
| Oral Mucositis | 660 | 50 mW | 8 J/cm$^2$ | |
| Oral Mucositis | 670 | 50 mW | 4 J/cm$^2$ | External application |
| Skin | | | 1-12 J/cm$^2$ | Rheumatoid Arthritis - anti inflammatory effect |
| Skin | 660 | 30 mW | 3-4 J/cm$^2$ | Wound |
| Skin | 632.8 | | 0.88 J/cm$^2$ | Fibroblast proliferation |

Phototherapy Doses in Animal Trials:

| Application | Dominant Wavelength | Power | Energy density | Comments |
|---|---|---|---|---|
| Oral Mucositis | 630 | 160 mW | 12 J/cm$^2$ | 37.5 seconds each session, 7 sessions |

-continued

| Application | Dominant Wavelength | Power | Energy density | Comments |
|---|---|---|---|---|
| Oral Mucositis | 660 | 30 mW | 1.2 J/cm$^2$ | 5 treatments, 40 seconds |
| Oral Mucositis | 880 | | 50 mW/cm$^2$ 4 J/cm$^2$ | 14 days |
| Other mucosa | 632 | | 8 mW/cm$^2$ 3.36 J/cm$^2$ | Rat Gastritis, 20 sessions of 420 seconds |
| Other mucosa | 632 | | 3.36 J/cm$^2$ | Rat colon anastomosis, 2 sessions |
| Skin | 820 | | 100 mW/cm$^2$ 2 J/cm$^2$ | Wound healing, single 20 seconds session |
| Skin | 635 | | 1, 5, 15 mW/cm$^2$ 5 J/cm$^2$ | Wound healing |
| Skin | 660 | 16 mW | 4 J/cm$^2$ | 4 sessions of 250 seconds |

Phototherapy Doses in In-Vitro Trials:

| Application | Dominant Wavelength | Power | Energy density | Comments |
|---|---|---|---|---|
| Oral Mucositis | 812 | | 4.5 mW/cm$^2$ 4 J/cm$^2$ | Fibroblast proliferation |
| Oral Mucositis | 880 | | 53 mW/cm$^2$ 8 J/cm$^2$ | |
| Oral Mucositis | 670 | | 4 J/cm$^2$ | |
| Skin | 809 | 10 mW | 1.96-7.4 J/cm$^2$ | Fibroblast proliferation, 1-3 sessions, 75-300 seconds each |

It is noted that phototherapy has not been performed in the small intestine for IBD, so no data is known to be available to determine appropriate medicine and/or dose values for small intestine LLLT.

It is noted that colon healing parameters are probably similar to small intestine healing values.

In some embodiments of the invention, suggested energy and dose for small intestine treatment are based on an average small intestine travel time. At an average GI tract length of 7 meters, and average travel time of 3-5 hours, a capsule's travel speed is estimated at an average rate of 0.065-0.039 cm/Sec.

Additional Portions of the GI Tract which May be Treated

In some embodiments of the invention, the stomach is treated. The capsule is swallowed and provides therapeutic illumination to the stomach. In some embodiments of the invention the capsule, after providing illumination, goes down the GI tract and is excreted.

In some embodiments of the invention, the colon is treated. The capsule is optionally inserted similarly to inserting a colonoscope, and provides therapeutic illumination to the colon.

In some embodiments of the invention, the colon is treated. The capsule is optionally inserted similarly to inserting a suppository, and provides therapeutic illumination to the colon.

Treatment Protocols

In some embodiments of the present invention, the following protocols are used to provide phototherapeutic treatment:

Treatment schedule: every other day; 3 times a week, and ranging from once a day to once a week.

Number of treatments: three treatment and up. It is noted that improvement upon providing NIR phototherapy has been detected after a third treatment, and that improvement upon providing phototherapy in any of the wavelengths listed herein is expected after a third treatment.

Duration of phototherapeutic illumination: duration of phototherapeutic illumination depends on a dose selected for the treatment. The duration is calculated taking into account the light intensity of the light sources and a measured and/or expected speed of movement along the GI tract, as is described further below.

Examples of dose/duration protocols which were used in mice experiments, some of which are described herein include:

| Dose (Joule/cm$^2$) | Exposure time (sec) | Distance (cm) | Wavelength |
|---|---|---|---|
| 1 | 60 | 0.5 | NIR |
| 0.5 | 30 | 0.5 | NIR |
| 0.25 | 15 | 0.5 | NIR |
| 0.1 | 6 | 0.5 | NIR |
| 1 | 30 | 0.5 | Red |
| 1 | 45 | 0.5 | Blue |

Energy Calculation

The following is an example energy density calculation of an example embodiment of a capsule as it travels through the small intestine. The example embodiment of the capsule which is presently described has a "light ring" around its circumference, produced by a re-shaping optics and/or by placing light sources around the capsule's surface, as in FIG. 6, light sources 176.

The "light ring" functions to make sure that therapeutic light is delivered to the intestine wall and not to an area in front and behind the capsule.

The size of the exemplary capsule, 11 mm in diameter by 27 mm length, relative to an inner diameter of the small intestine when empty, which is approximately 1 to 1.5 cm, dictates that the capsule typically travels in parallel to the intestine walls.

Total Treatment Energy

The therapeutic light emitted by the capsule is optionally energized by an internal battery located within the capsule. A theoretical maximal energy, to be supplied by the battery, may be calculated as follows:

$$\text{Bat\_total\_power} = I \cdot V \qquad \text{Equation 1}$$

where I is a continuous drain current from the battery, and V is the average battery voltage (battery voltage drops as the battery is exhausted). Battery capacity is measured by mAH (milli-Ampere Hour), so the battery capacity determines a duration during which a given current can be drained from the battery.

Battery theoretical energy can be defined by total Joule according to:

$$E = \text{Bat\_total\_power} \cdot \text{Discharge\_time} \qquad \text{Equation 2}$$

A maximal theoretical treated area is optionally calculated by using the required energy density (in Joule/cm2) for treatment, compared with a maximal theoretical energy provided by the battery:

$$\text{Treat\_area} = E/\text{Dose} \qquad \text{Equation 3}$$

A therapeutic digestible capsule is often limited by its capacity. The capsule cannot use large sized batteries.

By way of a typical example: an 80 mAh battery is used with a discharge voltage curve averaging at 3.6V. Using the formulas above, the maximal theoretical treated area:

$$\text{Treat\_area} = V \cdot I \cdot T/\text{Dose} \qquad \text{Equation 3:}$$

| Dose | 1 J/cm² | 0.5 J/cm² | 0.25 J/cm² | 0.1 J/cm² |
|---|---|---|---|---|
| Treat Area | 1,036 cm² | 2,073 cm² | 4,147 cm² | 10,360 cm² |

Due to losses from elements in electronic circuits in the capsule, and from therapeutic LEDs, the "real life" treated area may be lower. Some contributors to energy "loss" are:

DC to DC conversion and LED drivers, typical loss of about 15%;

LED efficiency, typical loss of about 70%; and control electronics, typical loss of about 5%.

It is noted that LED efficacy is dependent on a dominant wavelength of the LED.

Currently available Near Infra Red (NIR) or Red LEDs can show efficiency as stated above, 20%-30%. LEDs at other wavelengths can demonstrate a lower efficiency, such as a Blue LED which can demonstrate typical efficiency of 15%-20%.

In reality, a theoretical treatment area corresponding to 25% of the battery maximal energy is expected.

A simulation of the actual capsule performance has been conducted, yielding the following results for "real life" capsule treatment:

For a NIR LED treatment source—

| | Dose | | | |
|---|---|---|---|---|
| | 1 j/cm² | 0.5 J/cm² | 0.25 J/cm² | 0.1 J/cm² |
| 3 H peristaltic | 218 cm² | 431 cm² | 885 cm² | 2,212 cm² |
| 4 H peristaltic | 216 cm² | 433 cm² | 873 cm² | 2,164 cm² |

The simulation presented above is based on a capsule with a diameter of 11 mm, and an average small intestine of 15 mm diameter or less. Smaller intestine radius results in less required power for same dose, which saves battery power and increase treatment area covered by the light sources.

Area of Treatment

Typically, Crohn's Disease (CD) is a complete GI tract disease ("mouth to anus"). In most patients, Crohn's disease involves the small intestine, and in some patients, the large intestine is involved as well.

Most cases of CD involve the small intestine in general, and the terminal ileum in particular, a purpose of a capsule, as implemented in some embodiments of the invention, is to illuminate the entire small intestine if possible. If limited, for example by a limitation of treatment area, to partial coverage of the small intestine, then the terminal ileum is a priority area for treatment.

A typical entire small intestine is about 7 meters (700 centimeters) in length, with an average internal diameter of about 1.5 cm-2 cm. The terminal ileum length is about 2 m-4 m.

Using those dimensions, a treatment area can be calculated based on a simplified model of a tube:

$$\text{Area} = 2 \cdot \pi \cdot r \cdot h \qquad \text{Equation 4}$$

Based on the above, an entire small intestine average treated area is approximately 6,594 cm², and the terminal ileum treated area is approximately 2,826 cm².

In some embodiments of the invention, a capsule used in the small intestine, which has an average internal diameter of the intestine walls of 15 mm, is only slightly smaller than the intestine' diameter, or approximately 9 mm-11 mm. In most cases, during the peristaltic movement, the intestine walls are "collapsed" on the capsule, or very close to the capsule, which forces the capsule's orientation to be heading down the intestine with substantially little to no side movements.

Use of NIR wavelength allows for deep tissue penetration, up to 4 cm, which overcomes a need to have treated tissue in direct sight of the LED sources. Deep tissue penetration is associated with NIR and IR, and is reduced when wavelength shortens from Yellow to Blue and UV. The deep tissue penetration aids a capsule phototherapy to prevent folds in the intestine from interfering with phototherapeutic delivery to the intestine tissue.

An overlap of areas of treatment may cause an "over dose" of a certain overlap area and, as explained before, will show no effectiveness in this area. The activation mechanism of the light sources optionally acts to keep those overlap areas to a minimum.

Controlling Dose According to Travel Speed

In some embodiments of the invention, a dose is based on a multiplication of power and exposure time.

As the capsule travels through the intestine, it is subjected to varying travel speeds based on peristaltic action of the GI tract. The changing travel speeds change tissue exposure time—as a capsule travels faster it illuminates less per unit area of intestine.

In order to control delivery of an optimal dose to tissue, a control mechanism is included in some embodiments of the invention, designed to change illumination power according to travel speed.

A typical small intestine length in adult humans is 7 meters. Travel time through the small intestine varies between people and time of day, but in average is 3 to 5 hours.

Using the above average values, travel speed is calculated to be:

$$TravelSpeed = \frac{Intestine\_Length}{Travel\_Time} \quad \text{Equation 5}$$

For example, in case of a 3 hour travel time, speed is calculated as follows:

$$TravelSpeed = \frac{700[cm]}{3 \cdot 60 \cdot 60[sec]} = 0.0648[cm/sec] \quad \text{Equation 6}$$

The above calculation yields a travel speed of 0.0648 (cm/sec) to 0.0388 (cm/sec) for the 3 to 5 hours travel times.

According to a travel formula, where:

$$\text{Dist.} = \text{Speed} \cdot \text{Time} \quad \text{Equation 7}$$

Exposure time is a time which takes a capsule to travel over a defined distance, in this case a length of the "light ring", which is the effective area around the capsule which is illuminated by the LEDs.

$$Exposure\_time = \frac{Treatment\_length}{TravelSpeed} \quad \text{Equation 8}$$

Using the numbers above, the following exposure times, as a factor of travel speed and "ring" length, are obtained:

| Ring length/Travel time | 5 mm | 10 mm | 15 mm |
|---|---|---|---|
| 3 Hours | 7.7 Sec | 15.4 Sec | 23.1 Sec |
| 4 Hours | 10.3 Sec | 20.6 Sec | 30.8 Sec |
| 5 Hours | 12.9 Sec | 25.7 Sec | 38.6 Sec |

In the example embodiment now described, capsule optics and/or light source layout spreads therapeutic light substantially evenly across the "light ring". As there is substantially no "leakage" of therapeutic light outside the "light ring", the entire radiated therapeutic light, from the light source, is delivered to the "light ring" area of the inner intestine wall.

The surface area of the "ring" is given by:

$$Ring\_surface\_area = 2 \cdot \pi \cdot Ring\_length \cdot Intestine\_radius \quad \text{Equation 9}$$

Using some of the values calculated above, a typical "light ring" surface area is calculated as:

| Ring length/Intestine radius | 7.5 mm | 10 mm |
|---|---|---|
| 10 mm | 4.71 [cm$^2$] | 6.28 [cm$^2$] |
| 15 mm | 7.06 [cm$^2$] | 9.42 [cm$^2$] |

As described above, the radiated capsule power is delivered to the "light ring". The power density may be calculated by:

$$PowerDensity = \frac{Total\_Radiated\_Power}{Ring\_surface\_area} \quad \text{Equation 10}$$

Using the values for intestine radius and "light ring" length, the following radiated power densities are obtained:

| Total radiated power | 40 mW | 60 mW |
|---|---|---|
| Ring = 10 mm Intestine = 7.5 mm | 8.5 [mW/cm$^2$] | 12.7 [mW/cm$^2$] |
| Ring = 10 mm Intestine = 10 mm | 6.3 [mW/cm$^2$] | 9.5 [mW/cm$^2$] |
| Ring = 15 mm Intestine = 7.5 mm | 5.6 [mW/cm$^2$] | 8.5 [mW/cm$^2$] |
| Ring = 15 mm Intestine = 10 mm | 4.2 [mW/cm$^2$] | 6.3 [mW/cm$^2$] |

The energy density of the therapeutic light is a multiplication of the power density and the exposure time of a given point in the small intestine.

When using all the above calculations, one example of energy densities for an example operating scenario is obtained:

Intestine radius—5 mm
Ring length—10 mm
Treatment area for this setup is 3.14 cm$^2$

| Travel duration | Speed | Exposure time | Radiated power | Power density | Energy density |
|---|---|---|---|---|---|
| 3 hours | 0.0648 cm/sec | 15.4 sec | 40 mW | 12.7 mW/cm$^2$ | 0.20 J/cm$^2$ |
| 4 hours | 0.0486 cm/sec | 20.6 sec | 40 mW | 12.7 mW/cm$^2$ | 0.26 J/cm$^2$ |
| 5 hours | 0.0388 cm/sec | 25.7 sec | 40 mW | 12.7 mW/cm$^2$ | 0.33 J/cm$^2$ |
| 3 hours | 0.0648 cm/sec | 15.4 sec | 60 mW | 19.1 mW/cm$^2$ | 0.29 J/cm$^2$ |
| 4 hours | 0.0486 cm/sec | 20.6 sec | 60 mW | 19.1 mW/cm$^2$ | 0.39 J/cm$^2$ |
| 5 hours | 0.0388 cm/sec | 25.7 sec | 60 mW | 19.1 mW/cm$^2$ | 0.49 J/cm$^2$ |

Summarizing principles of operation of the control mechanism, the following inputs are some which affect the dose radiated to tissue:

LED power—output of the control mechanism, by direct control over LED average current or by modulating the LED;

Peristaltic, or travel speed—Travel speed is optionally measured by a capsule accelerometer or a similar mechanism;

Intestine radius is assumed to be 7.5 mm for the small intestine, and 15 mm for the large intestine;

Ring length—determined during design of a capsule. An example embodiment of a first generation capsule has a 10 mm ring length; and Dose required (in J/cm2).

The control formulae may now be expressed approximately as:

$$Exposure\_time = Ring\_length/(Intestine\_Length/(Intestine\_Speed*60*60)); \quad \text{Equation 11}$$

$$Power\_density = Dose/Exposure\_time; \quad \text{Equation 12}$$

Required_Power=Power_density*
(2*π*Radius*Ring_length); Equation 13

In some embodiments of the invention, when a physician plans a Dose to be applied for phototherapy, and knows an expected average Intestine_Speed, the physician optionally applies equation 14 below, which is a result of equations 11, 12, and 13 above, and which is an approximation of the required power for providing the Dose to a diseased area:

Required_Power=Dose*(Intestine_Length/(Intestine_
Speed*60*60))(2*z*Radius); Equation 14

In some embodiments of the invention, the Required_Power calculation above is written as:

Required_Power=C*Dose/Intestine_Speed; Equation 15

Where C is a constant calculated using the numbers of equation 14 and an expected value for a Radius of a patient's diseased portion of the GI tract. The constant C is optionally provided as a lookup table for a physician and or medical practitioner, for different values of Radius.

In some embodiments of the invention, a capsule is optionally programmed with a value for C, a Dose value, and the capsule optionally senses Intestine_Speed, enabling the capsule to calculate Required_Power according to equation 15.

In some embodiments of the invention the capsule is programmed to provide an effective dose by providing power over a minimal threshold, and below an overdose. For example, in cases where a high intestinal speed, more power is supplied.

When the capsule senses that Required_Power is higher than a threshold value, the threshold value being set to limit the Required_Power to being effective and not reach an overdose, the capsule may be programmed to turn the light sources OFF.

In some embodiments of the invention, after the capsule has optionally turned the light sources OFF, when the capsule senses a movement along the GI tract equal to a Ring_length, and if the capsule is still within a segment of the GI tract programmed for treatment, the capsule optionally turns the light sources ON.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

It is noted, and the above description teaches, that in some cases a capsule cannot provide illumination therapy to all of a diseased GI tract.

As described above, in some embodiments of the invention, the capsule turns therapeutic illumination on at a certain point in its journey through the GI tract, and turns the therapeutic illumination off, or possibly runs out of power to run the therapeutic illumination, later in its journey through the GI tract.

Figure 20A:
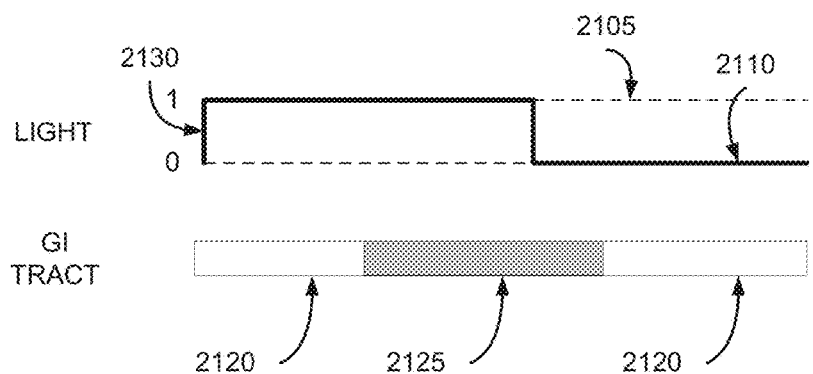

Reference is now additionally made to FIG. 20A, which is a simplified diagram of a length of a GI tract 2120, and a corresponding diagram 2130 of a first example of when light source(s) in a capsule are turned ON 2105 and OFF 2110.

The GI tract diagram also depicts a diseased portion 2125 of the GI tract 2120.

The diagram 2130 indicates when a capsule's illumination is turned on (the diagram 2130 runs along the ON line 2105) and turned off (the diagram 2130 runs along the OFF line 2110).

FIG. 20A depicts, in the first example, a capsule which emits light as it is swallowed, and emits light for a first portion of its travel along the GI tract 2120.

FIG. 20A depicts a problem case, where the diseased portion 2125 of the GI tract 2120 starts later than the beginning of the GI tract 2120, and extends further than the capsule provides therapeutic illumination, whether because of running out of power, or because of improper timing of when the therapeutic illumination should be ON.

Figure 20B:
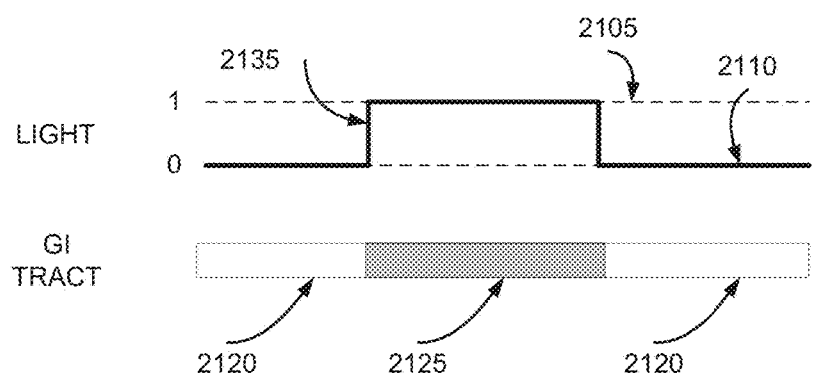

Reference is now additionally made to FIG. 20B, which is a simplified diagram of a length of a GI tract 2120, and a corresponding diagram 2135 of a second example of when light source(s) in a capsule are turned ON 2105 and OFF 2110.

The GI tract diagram also depicts a diseased portion 2125 of the GI tract 2120.

The diagram 2135 indicates when the capsule's illumination is turned on (the diagram 2135 runs along the ON line 2105) and turned off (the diagram 2135 runs along the OFF line 2110).

FIG. 20B depicts, in the second example, a capsule which emits light some time after it is swallowed, and emits light for some portion of its travel along the GI tract 2120.

FIG. 20B depicts a case of well designed therapy, where the therapeutic illumination is emitted from the capsule all along the diseased portion 2125 of the GI tract 2120. A beginning of the therapeutic illumination is substantially at a beginning of the diseased portion 2125, and the diseased portion 2125 either turns off or loses power at the end of the diseased portion 2125. The good overlap of the therapeutic illumination being ON and the diseased portion 2125 of the GI tract is achieved by any one of the methods described above for turning ON the light sources, be it setting a timer, and/or starting the timer by environmental sensing, and/or sensing a location, and so on.

An example medical case suitable for the example of FIG. 20B can be treating the area of the terminal ileum, without treating the preceding GI tract.

Figure 20C:
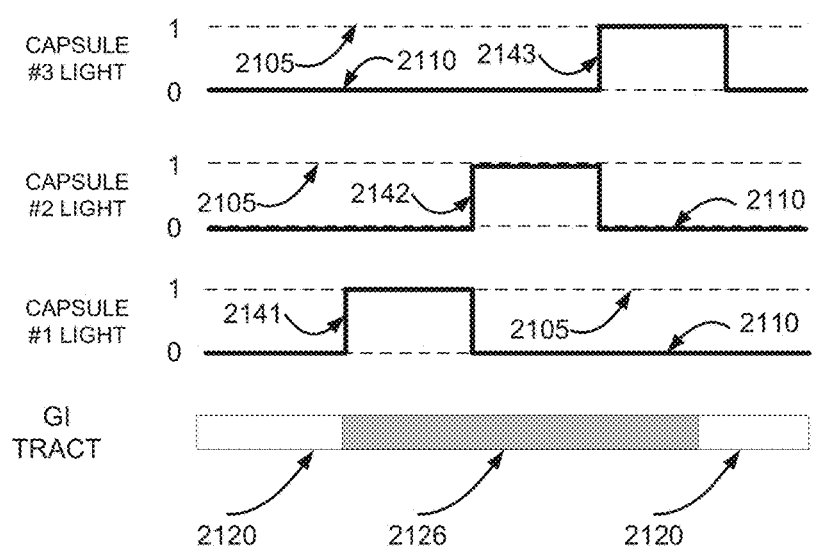

Reference is now additionally made to FIG. 20C, which is a simplified diagram of a length of a GI tract 2120, and corresponding diagrams 2141 2142 2143 of a third example of when light source(s) in capsules are turned ON 2105 and OFF 2110.

The GI tract diagram also depicts a diseased portion 2126 of the GI tract 2120.

FIG. 20C depicts, in the third example, a set of three capsules, each of which emits light some time after it is swallowed, and emits light for some portion of its travel along the GI tract 2120.

The diagram 2141 indicates when a first capsule's illumination is turned on (the diagram 2141 runs along the ON line 2105) and turned off (the diagram 2141 runs along the OFF line 2110). The diagram 2142 indicates when a second capsule's illumination is turned on (the diagram 2142 runs along the ON line 2105) and turned off (the diagram 2142 runs along the OFF line 2110). The diagram 2143 indicates when a third capsule's illumination is turned on (the diagram 2143 runs along the ON line 2105) and turned off (the diagram 2143 runs along the OFF line 2110).

FIG. 20C depicts a case of well designed therapy, where the therapeutic illumination is emitted from the three capsules all along the diseased portion 2125 of the GI tract 2120.

Figure 20D:
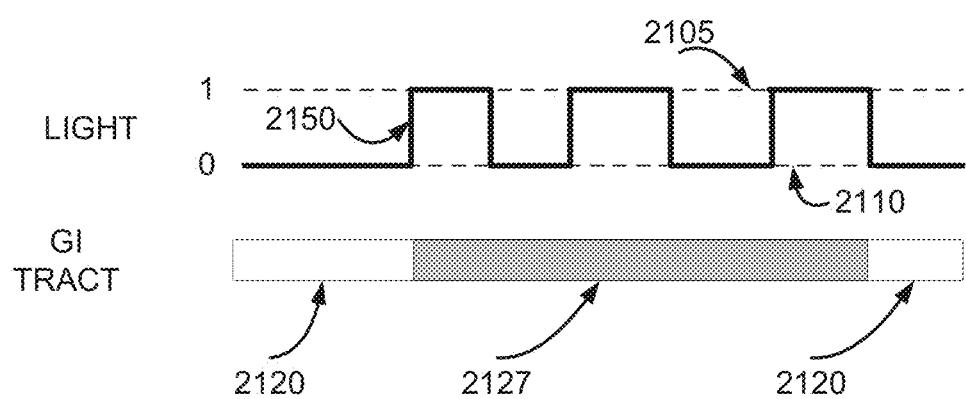

Reference is now additionally made to FIG. 20D, which is a simplified diagram of a length of a GI tract 2120, and a corresponding diagram 2150 of a fourth example of when light source(s) in a capsule are turned ON 2105 and OFF 2110.

The GI tract diagram also depicts a diseased portion 2127 of the GI tract 2120.

The diagram 2150 indicates when the capsule's illumination is turned on (the diagram 2150 runs along the ON line 2105) and turned off (the diagram 2150 runs along the OFF line 2110).

FIG. 20D depicts, in the fourth example, a capsule which cycles emitting light ON and OFF, beginning some time after it is swallowed, over a portion of its travel along the GI tract 2120.

The capsule cycles providing the therapeutic illumination for any one of several reasons, some of which are:

It may be desirable to limit the therapeutic illumination at a section, so as not to overdose. If travel of the capsule is slow so that providing continuous illumination causes an overdose, the capsule optionally cycles the illumination, thus lowering the dose per unit length/unit area.

In some cases, where a GI tract disease is detected at several locations along the GI tract, the light sources are optionally turned ON at the disease locations, and OFF at locations which do not display a disease.

It may be that the capsule does not have enough power to last all along a diseased section of the GI tract. An example medical case could be treating Crohn's disease, where the entire GI tract is affected. Treatment, in some embodiments of the invention, is provided at limited-length sections all along the GI tract. In some embodiments of the invention, modulation of the LED light intensity, and/or turning LEDs ON and OFF, is optionally used to affect LED average output power by changing the LEDs' duty cycle.

It is expected that during the life of a patent maturing from this application many relevant power supplies, light sources, and medical imaging systems will be developed, and the scope of the terms power supplies, light sources, and medical imaging systems is intended to include all such new technologies a priori.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

The following examples are provided for illustrative purposes and in order to more particularly explain and describe the present invention. The present invention, however, is not limited to the particular embodiments disclosed in these examples.

EXAMPLES

Reference is now made to the following examples, which together with the above descriptions illustrate some embodiments of the invention in a non limiting fashion.

Example 1

An Example Phototherapy Capsule of the Present Invention

Physical dimensions—Length 27 mm

External diameter 11 mm

The outer shell is transparent and is made of a mixture of Polycarbonate, Polystyrene and K-resin with a wall thickness of 0.4 mm, and is manufactured using a conventional molding technique as well known to the skilled artisan.

The power source contained within the capsule is a small cylindrical battery—for example GP1015L08—having a length of 15 mm and a diameter of 10 mm.

The capsule includes 2 electronic printed circuit boards, the first of which is a DC to DC boost converter (Texas Instrument's TPS61041) used to drive the LEDs used in the capsule, and a controlling microprocessor (MicroChip's PIC12F1822-I/MF) which controls the activation and operation of the capsule.

The second circuit hosts the Photo-therapy LEDs in a circular arrangement, such that the light generated by said LEDs is transmitted radially outwards.

The LEDs are UT-692UR supplied by L.C LED and provide light centered at 660 nm.

As part of the capsule's shell, above the LEDs, is a beam-shaping optics which re-shapes the LEDs radiated energy into a uniform "ring" shaped beam around the capsule. The optics are incorporated into the capsule's transparent shell and are designed as a "ring" surrounding the area of the LEDs. The optics are designed to concentrate the beam on the capsule's longitude axis while not affecting the radial axis beam. The capsule also comprises a small accelerometer (ADXL337 manufactured by Analog Devices) connected to the above-mentioned controlling microprocessor.

Example 2

Effect of Intraluminal Phototherapy in a Murine Colitis Model

Introduction:

A dextran sulfate sodium (DSS)-induced colitis model in mice was used to demonstrate the positive therapeutic effect obtained by using intraluminal phototherapy to treat inflammatory lesions of the GI tract. Colitis was induced in C57BL/6 mice by adding DSS to their drinking water, in accordance with standard protocols for chronic and acute DSS-induced colitis [Wirtz et al., 2007, Nature Protocols Vol. 2 pp. 541-546]. Phototherapy treatment was carried out using a Storz mini-endoscope system fitted with intraluminal light sources emitting at 440±40 nm (blue), 660±50 nm (red) and 850±50 nm (near infra-red [NIR]). Severity of the induced colitis was assessed endoscopically using the following set of criteria:

| Murine endoscopic index of colitis severity | | | | | |
|---|---|---|---|---|---|
| | 0 | 1 | 2 | 3 | Total |
| Thickening of the colon | Transparent | Moderate | Marked | Non-transparent | 0-3 |
| Changes of the vascular pattern | Normal | Moderate | Marked | Bleeding | 0-3 |
| Fibrin visible | None | Little | Marked | Extreme | 0-3 |
| Granularity of the mucosal surface | None | Moderate | Marked | Extreme | 0-3 |
| Stool consistency | Normal + solid | Still shaped | Unshaped | Spread | 0-3 |
| | | | | | Overall: 0-15 |

Experimental design: acute DSS colitis was induced in 44 mice, which were then allocated to one of four treatment groups (each containing 11 mice): two treatment groups (A and B), sham treatment (no light used) and control, in accordance with the protocol shown in the following table:

| | Duration of each phototherapy session (min.) | Frequency of treatments (session/week) | Light source wavelength | Irradiation intensity (j/cm2) |
|---|---|---|---|---|
| A | 7 | 2 | NIR | ~1 |
| B | 3.5 | 2 | red | ~1 |
| Sham | 3.5 | 2 | No light | — |
| Control | No phototherapy No treatment | — | — | — |

During the treatment phase (groups A, B and sham), the colonoscope was inserted into the colon as far as the splenic flexure, and then pulled out gradually to simulate the movement of an ingested capsule device. The following table presents the results for disease severity assessed at three different time points (measured from day zero of the study)—Day 9, Day 13 and Day 19:

| Group | Day 9 | Day 13 | Day 19 |
|---|---|---|---|
| A | 7.29 ± 0.76 | 9.57 ± 2.30 | 9.60 ± 2.07 |
| B | 7.60 ± 1.14 | 9.20 ± 2.59 | 9.60 ± 2.30 |
| Sham | 10.00 ± 1.26 | 11.50 ± 2.07 | 11.00 ± 0.63 |
| Control | 9.60 ± 0.89 | 12.40 ± 2.07 | 12.00 ± 1.00 |

When the results for treatment groups A and B were taken together, the reduction in disease severity in the phototherapy-treated animals in relation to the sham group was statistically significant at each of the three time-points.

The results of this study demonstrate that intraluminal phototherapy is effective in significantly reducing the severity of colitis in a mouse.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A programmable system for providing phototherapy to a patient's gastrointestinal (GI) tract, said system comprises at least one swallowable capsule, said capsule comprising:
   a power supply;
   at least one phototherapeutic light source configured to emit light at at least one wavelength in a range selected from a group consisting of visible light, Near Infra Red (NIR) light and any combination thereof;
   a speed determination unit for determining speed of movement of the capsule at at least one target site in the GI tract;
   a controller unit for controlling illumination by said at least one phototherapeutic light source to provide an effective phototherapeutic illumination dose in a range of 0.1-1.0 Joules/cm$^2$ and for activating at least one of the at least one phototherapeutic light source for delivering said effective phototherapeutic illumination dose to said at least one target site, and
   at least one processor controlling instructions for said controller unit operation;
   wherein said processor is programmed to instruct said controller to calculate distance travelled along the GI tract, according to measured said speed of movement, and to turn ON said light source at at least one target site according to said distance travelled, said effective illumination dose is calculated by said processor according to the following formula:

Required Power=C*Dose/Intestine Speed, in which

C is a constant programmed in the controller;
   Dose is a constant programmed in the controller; and
   Intestine Speed is the speed of movement of the capsule in the GI tract.

2. The capsule according to claim 1, wherein, if the speed determination unit determines a capsule speed which is zero, the controller unit is configured to cause the controller unit to turn said at least one phototherapeutic light source OFF.

3. The capsule according to claim 1, wherein intensity of at least one of said at least one phototherapeutic light source is adjustable based, at least in part, on said determined speed of movement of the capsule at said at least one target site in the GI tract.

4. The capsule according to claim 1, wherein said at least one phototherapeutic light source emits light at a wavelength in a range selected from a group consisting of 610-750, 800-950 nm and any combination thereof.

5. The capsule according to claim 1, wherein said at least one phototherapeutic light source emits light centered at a wavelength selected from a group consisting of 660 nm, 850 nm and any combination thereof.

6. A method for providing phototherapy to a portion of a GI tract comprising:
   swallowing at least one capsule, said capsule comprising:
      at least one phototherapeutic light source configured to emit light at at least one wavelength in a range selected from a group consisting of visible light, Near Infra Red (NIR) light and any combination thereof;
      a speed determination unit for calculating speed of movement of the capsule in the GI tract,
      a controller unit for controlling illumination by at least one of said at least one phototherapeutic light source so as to provide an effective phototherapeutic illumination dose to be in a range of 0.1-1.0 Joules/cm$^2$ and for activating at least one of the at least one phototherapeutic light source for delivering said effective phototherapeutic illumination dose to said at least one target site, and
      at least one processor controlling instructions for said controller unit operation;
   wherein said processor is programmed to instruct said controller to calculate distance travelled along the GI tract, according to measured said speed of movement, and to turn ON said light source at at least pre-defined target area according to said distance travelled, said effective illumination dose is calculated by said processor according to the following formula:

Required Power=C*Dose/Intestine Speed, in which

C is a constant programmed in the controller;
   Dose is a constant programmed in the controller; and
   Intestine Speed is the speed of movement of the capsule in the GI tract.

7. The method according to claim 6, wherein the effective phototherapeutic illumination dose is in a range of 0.25-0.5 Joule/cm$^2$.

8. The method according to claim 6, wherein said at least one phototherapeutic light source is turned off when the capsule computes a speed of the capsule which indicates that the capsule has stopped.

9. The method according to claim 6, wherein said at least one phototherapeutic light source emits light at a wavelength in a range selected from a group consisting of 610-750 nm, 800-950 nm and any combination thereof.

10. The method according to claim 6, wherein said at least one phototherapeutic light source emits light centered at a wavelength selected from a group consisting of 660 nm, 850 nm and any combination thereof.

11. The method according to claim 6, wherein the intraluminal phototherapy of the gastrointestinal (GI) tract is administered at a schedule selected from a group consisting of: every other day; three times a week, and ranging from once a day to once a week.

12. The method according to claim 6, wherein the intraluminal phototherapy of the gastrointestinal (GI) tract is administered a plurality of times.

13. The method according to claim 6, wherein the intraluminal phototherapy of the gastrointestinal (GI) tract is administered three times or more.

14. The method according to claim 6, wherein the method is used to treat inflammatory bowel disease selected from a group consisting of Crohn's disease; ulcerative colitis; and indeterminate colitis.

15. The method according to claim 6, wherein the method is used to promote healing of the intestinal mucosa and submucosal tissues.

16. The method according to claim 6, additionally comprising a step of controlling activation of said at least one phototherapeutic light source when the capsule is in proximity to at least one of said at least one target site in the gastrointestinal (GI) tract so as to provide said effective phototherapeutic illumination dose to said at least one of said at least one target site of the GI tract, based, at least in part, on a determined speed of movement of the capsule at said at least one of said at least one target site of the GI tract.

17. The capsule according to claim 1, wherein said at least one region of said GI tract is identifiable from a member of a group consisting of: a distance traveled along said GI tract; a change in speed of movement of the capsule; a change in pH of the environment of the capsule, an average speed of movement of said capsule, a distance from said capsule to a wall of said GI tract and any combination thereof.

18. The method according to claim 6, additionally comprising a step of identifying said at least one region of said GI tract from a member of a group consisting of: a distance traveled along said GI tract; a change in speed of movement of the capsule; a change in pH of the environment of the capsule, an average speed of movement of said capsule, a distance from said capsule to a wall of said GI tract and any combination thereof.

19. The system of claim 1, wherein said power supply is a battery, said battery is located within said capsule.

20. The system of claim 1, wherein said capsule speed is determined by a motion detecting means.

21. The claim motion means of claim 20, wherein said motion means is selected from a group consisting of an accelerometer, or an optical motion sensing system.

22. The system of claim 1, wherein said system comprises a plurality of said capsules, wherein each of said capsules is programmed with different controlling instructions.

23. The system of claim 1, wherein said at least one GI target of at least one capsule is pre-programmed according to at least one diseased GI region of said patient.

24. The system of claim 1, said system comprises a plurality of said capsules, wherein each of said capsules is programmed with a different delay time, a different exposure time or a different location; said plurality of capsules configured to provide phototherapy to at least one target sites of a patient's GI tract while maintaining relatively low power consumption for each of said capsule.

* * * * *